US007468788B2

(12) United States Patent  (10) Patent No.: US 7,468,788 B2
Gibbs et al. (45) Date of Patent: Dec. 23, 2008

(54) SYSTEMS AND METHODS FOR CHIRAL DETECTION AND ANALYSIS

(75) Inventors: Phillip R. Gibbs, Atlanta, GA (US); John Wade, Alpharetta, GA (US)

(73) Assignee: Stheno Corporation, Atlanta, GA (US)

( * ) Notice: Subject to any disclaimer, the term of this patent is extended or adjusted under 35 U.S.C. 154(b) by 366 days.

(21) Appl. No.: 11/471,994

(22) Filed: Jun. 21, 2006

(65) Prior Publication Data

US 2007/0008530 A1 Jan. 11, 2007

(51) Int. Cl.
*G01N 21/01* (2006.01)
*G01J 4/00* (2006.01)
(52) U.S. Cl. .................. 356/244; 356/245; 356/364
(58) Field of Classification Search ......... 356/244–246, 356/364–369
See application file for complete search history.

(56) References Cited

U.S. PATENT DOCUMENTS

| 4,011,451 | A |   | 3/1977  | Nelson |   |
|-----------|---|---|---------|--------|---|
| 4,276,475 | A |   | 6/1981  | Nelson |   |
| 4,313,679 | A | * | 2/1982  | Wolff et al. ................ 356/244 |
| 4,467,204 | A |   | 8/1984  | Kysilka et al. |
| 4,699,514 | A | * | 10/1987 | Schmidt et al. ............. 356/367 |
| 5,168,326 | A |   | 12/1992 | Tokieda et al. |
| 5,822,067 | A |   | 10/1998 | Yanik |
| 6,046,804 | A |   | 4/2000  | Kawamura et al. |
| 6,307,204 | B1 |  | 10/2001 | Kanomata et al. |
| 6,717,665 | B2 | * | 4/2004 | Wagner et al. .............. 356/244 |
| 2003/0174323 | A1 | | 9/2003 | Wagner et al. |

FOREIGN PATENT DOCUMENTS

JP   2000 292347   10/2000
WO   WO 2005/036215   4/2005

* cited by examiner

*Primary Examiner*—L. G Lauchman
(74) *Attorney, Agent, or Firm*—Finnegan, Henderson, Farabow, Garrett & Dunner LLP

(57) ABSTRACT

Relating to chiral detection systems, various improvements are disclosed including an improved apparatus for detecting a chiral property of a sample. It has a rugged and stable optical rail that operates as a heat sink to the systems' elements and comprises a captive guide structure of heat conductive material having an elevated top platform and a dove tailed lip on the sides. The elevated top platform has a substantial width in comparison to a height of the elevated top platform. The apparatus further includes a wide base portion of heat conductive material supportive of the captive guide structure. The base has a width that is at least twice the width of the elevated top platform and a substantial thickness relative to the captive guide structure. Multiple system elements can be securely mounted on the captive guide structure with some elements being in thermal contact with the elevated top platform.

8 Claims, 41 Drawing Sheets

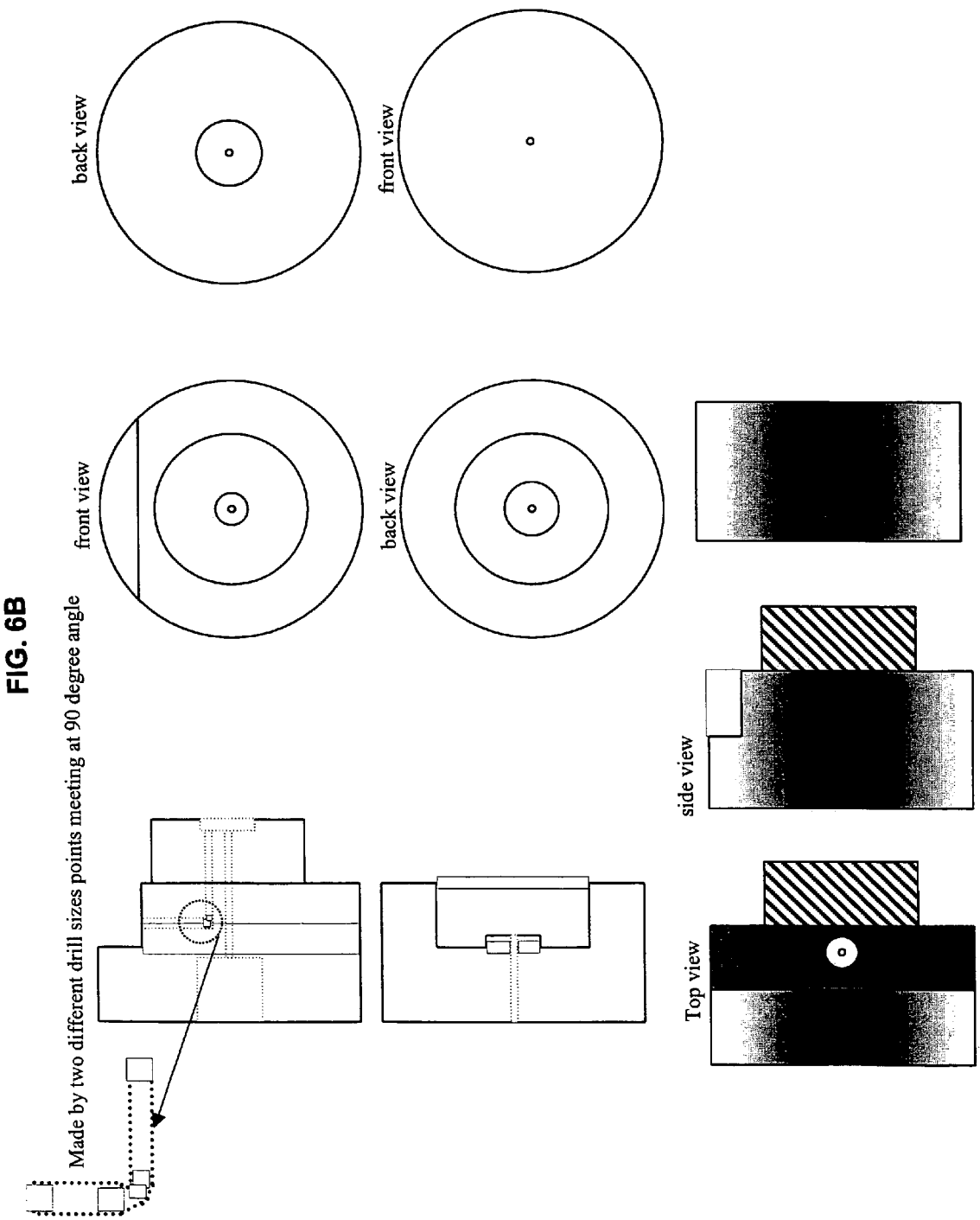

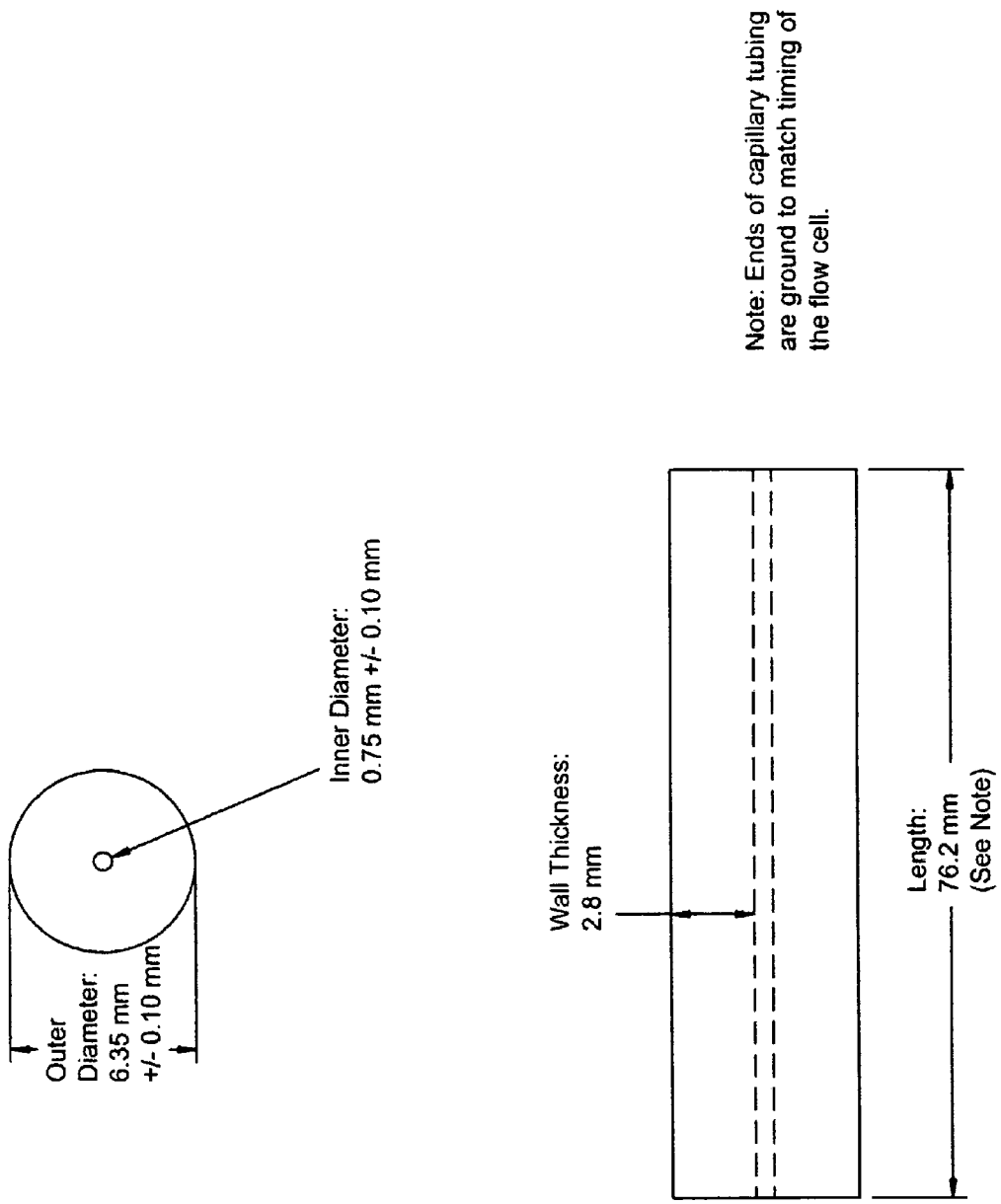

FIG. 6D
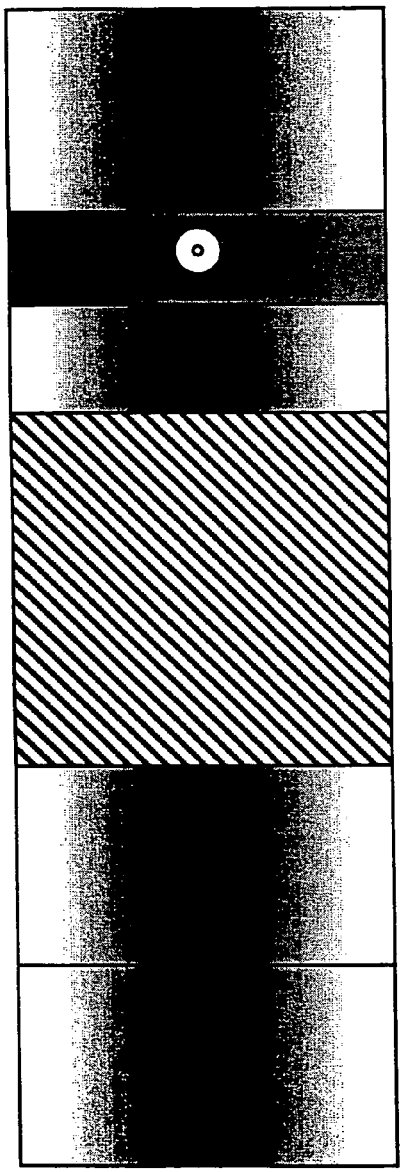
Assembled flow cell bobbin with coil
Top view
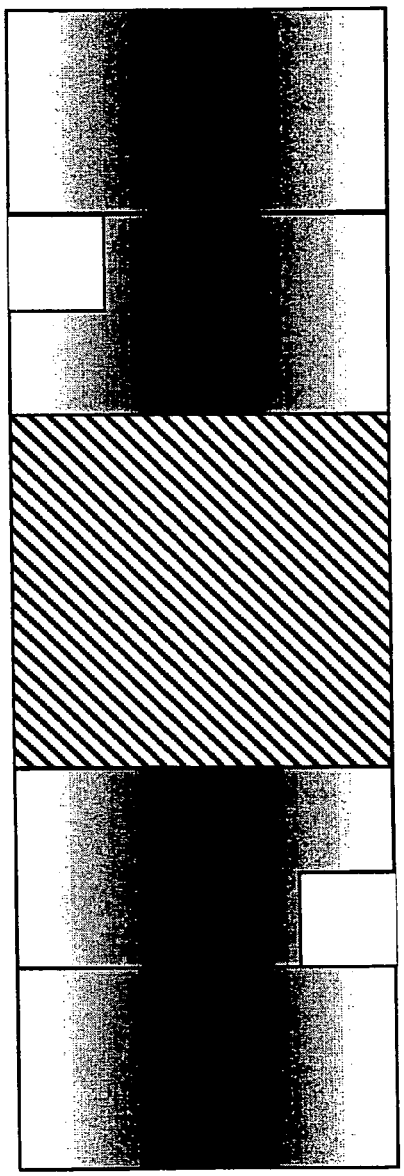
Assembled flow cell bobbin with coil
Side View

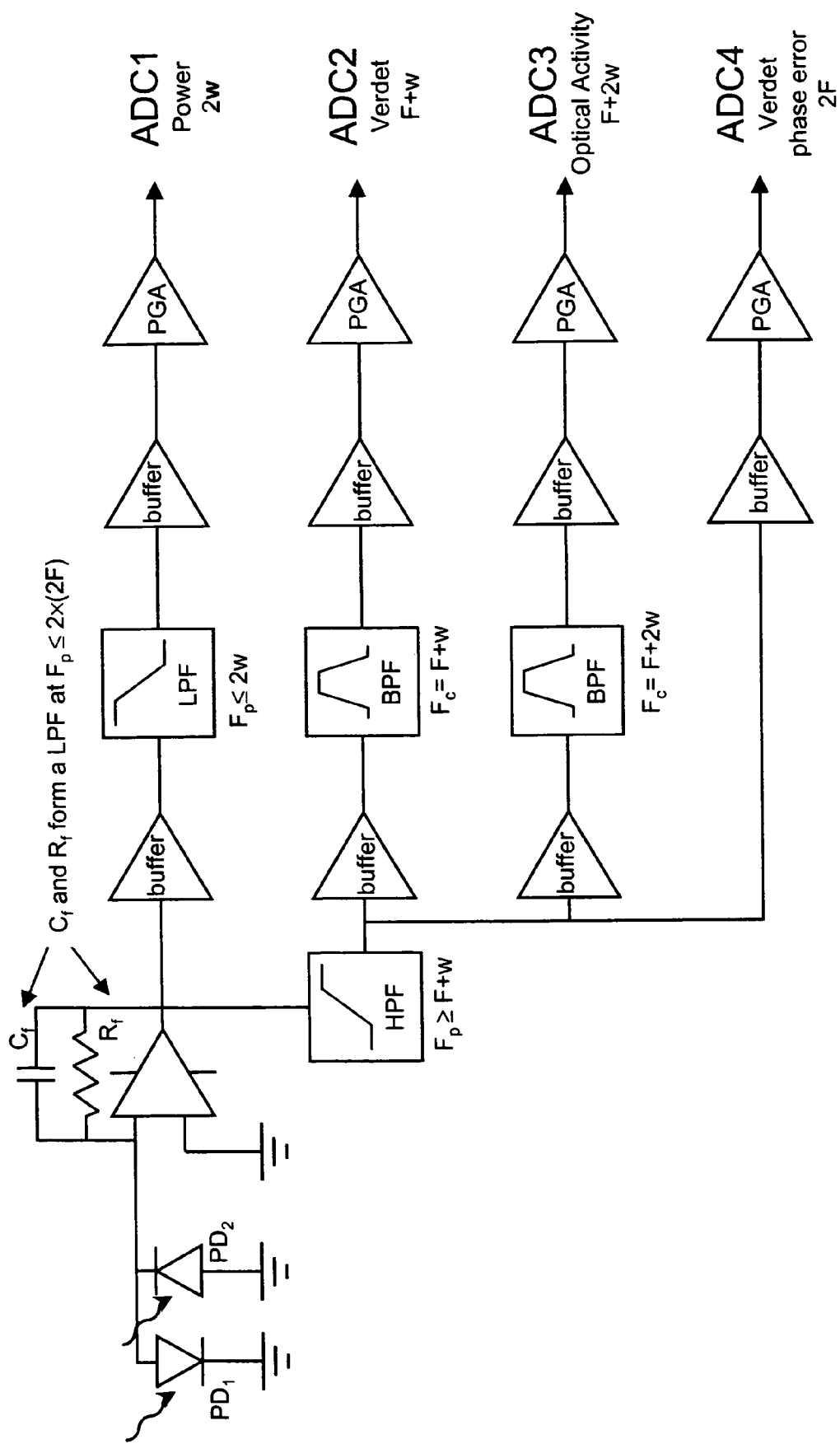

FIG. 10

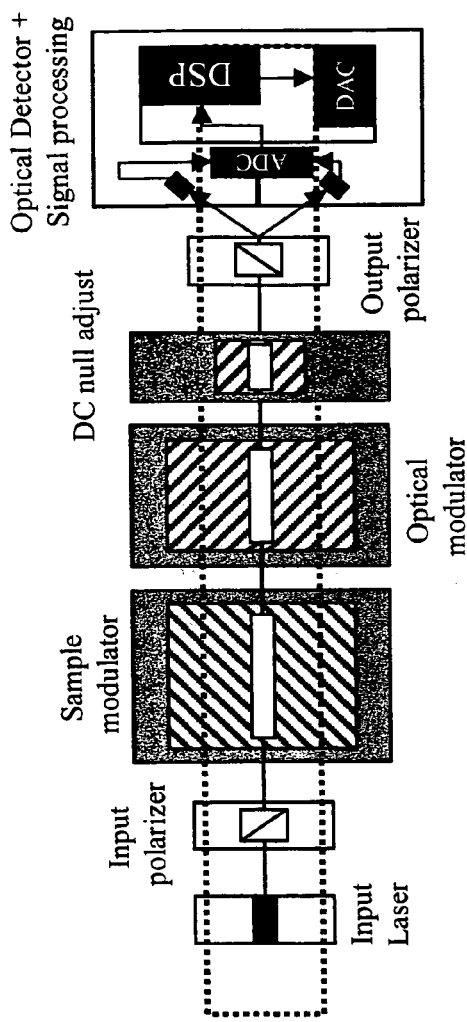

Note: The components between the polarizers can be arranged in any order but due to the larger acceptance angle of the optical modulator and DC null adjust, these elements usually follow the sample modulator cell in the beam path. For the 45 degree filtering scheme with laser modulation, the optical modulator block is removed and the overall rail length is reduced.

FIG. 14 Differential Photovoltaic detectors

SYSTEMS AND METHODS FOR CHIRAL DETECTION AND ANALYSIS

FIELD OF INVENTION

The present invention relates to chiral detectors, more particularly to an improved sample cell-based system for non-contact, rapid, low-noise and accurate screening of chiral samples.

BACKGROUND OF THE INVENTION

In general, a "chiral" object is one that is not superimposable upon its mirror image. In other words, a chiral object and its mirror image are similar in constitution or content, but different in orientation. Examples of chiral objects include a human hand, a mechanical screw, or a propeller. While they the mirror images look similar, they have different characteristic orientations with regard to their parts (e.g., the digits on the hand, the helical orientation of the screw, and the pitch orientation of the blades on the propeller).

In stereochemistry, two forms of a chiral object (such as a molecule) are also known as enantiomers, which is a type of stereoisomer. Enantiomers have the same chemical purity (e.g., the same mass, absorbance, refractive index, Verdet constant, etc.) but have different configurations in symmetry or symmetric properties. A collection containing only one enantiomeric form of a chiral molecule is often referred to as enantiopure, enantiomerically pure, or optically pure. However, unlike other stereoisomers, enantiomers are often difficult to separate and quantitate.

Detection of chiral molecules has become of increasing interest to the pharmaceutical industry over the last twenty years. This interest is driven at least in part by the common occurrence of drastically different pharmacological activities between enantiomers. The different pharmacological activity associated between enantiomers often requires that the drug be produced as a single chiral isomer. This single chiral isomer would be selected as it would have the most beneficial effects or, in some cases, would not have dangerous pharmacological activity. However, analytical methods for assaying enantiomeric purity have not kept pace with the increasing demands for rapid, high sensitivity, enantiomeric analysis. To date no generally applicable method for high throughput enantiomeric purity screening is available to the researcher.

There are known improvements to chiral analysis techniques, more specifically, in the area of reducing noise associated with the measurement of the additional optical rotation induced by a chiral sample. Single beam methods utilizing electronic or optical means to filter noise are quite common (see, for example, WO 01/06918). Other known methods utilize dual beams either by comparison to a reference cell (U.S. Pat. No. 4,912,059), mixing out of phase sinusoidal signals (U.S. Pat. No. 5,477,327), switching between a signal and reference beam (U.S. Pat. No. 5,621,528), or using a two frequency laser source with two orthogonal linear polarized waves (U.S. Pat. Nos. 5,896,198 and 6,327,037). These methods attempt to determine the displacement from the null point of optical transmission.

It is also known to use pockels cell modulation for differential chiral analysis in flow cells (U.S. Pat. No. 5,168,326). This technology involves the application of oscillating voltage to the pockels cell to produce alternating beams of linearly polarized light and circularly polarized light. By subtracting the rotation angles calculated for both beams, common sources of noise are effectively canceled out, giving a more sensitive measurement.

Thus, there remains a need for systems and methods that more accurately determine the chiral purity of a sample.

SUMMARY OF THE INVENTION

Relating to chiral detection systems, various improvements are disclosed. In one aspect, an improved optical rail is disclosed that is increased in size so as to operate as a heat sink to the systems' optical elements. In another aspect, an improved sample modulator is disclosed made in a dual clam shell configuration with breaks that disrupt eddy current heating, aid in the alignment of the sample cell, hold the sample cell within it, operates as a heatsink, and functions to contain the fields and minimize undesired cross-talk between modulators in the system. In another aspect, an improved sample flow cell is disclosed that conformally fits within the halves of the sample modulator and with an input chamber for rapid mixing the solvent. In another aspect, an improved nulling process and DC nulling device or module is disclosed that provides a precision level of DC adjustment to the field and improved analytical processing of the detected signals to provide more accurate and more detail information about the chiral purity of the sample being tested within the system. Such a nulling device or null adjust provides an internal standard that, once zeroed, sets the current and provides a known positive rotation and can provide multiple points if needed given the multi-bit resolution on the constant current DC source. In yet another aspect, a filtering and DSP analysis scheme is disclosed for generating a signal output. For example, such schemes may implement digital filtering (ideal HP, LP, BP) and more complex filtering schemes, such as Kalman filtering.

Additional aspects of the invention will be set forth in part in the description which follows, and in part will be obvious from the description, or may be learned by practice of the invention. Aspects of the invention will be realized and attained by means of the elements and combinations particularly pointed out in the appended claims. Therefore, it is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIGS. 6A-D are diagrams of additional embodiments of tubing and the sample flow cell in accordance with principles of the present invention.

FIGS. 9A-9F are diagrams of exemplary photodetector and filtering schemes in accordance with principles of the present invention.

FIG. 10 is an embodiment of the chiroptical detection system that uses a DC null adjust module in the receiver path of the system in accordance with an embodiment of the present invention.

DESCRIPTION OF THE EMBODIMENTS

Reference will now be made in detail to the present exemplary embodiments of the invention, examples of which are illustrated in the accompanying drawings, presentations, specifications and other technical documentation. Wherever possible, the same reference numbers will be used throughout the drawings to refer to the same or like parts.

In general, FIGS. 1, 2, 10 and 15 illustrate exemplary chiral detection systems and operating environments for such systems according to embodiments of the present invention. The systems shown in these figures provide an environment in which various chiral detection improvements have been made as will be described further herein. For example, improved features of a chiral detection system, such as an improved optical rail, an improved sample modulator, an improved sample flow cell, improved nulling, and improved analytical processing of the detected signals, are described below to address the need for systems and methods that more accurately determine the chiral purity of a sample.

Figure 1:
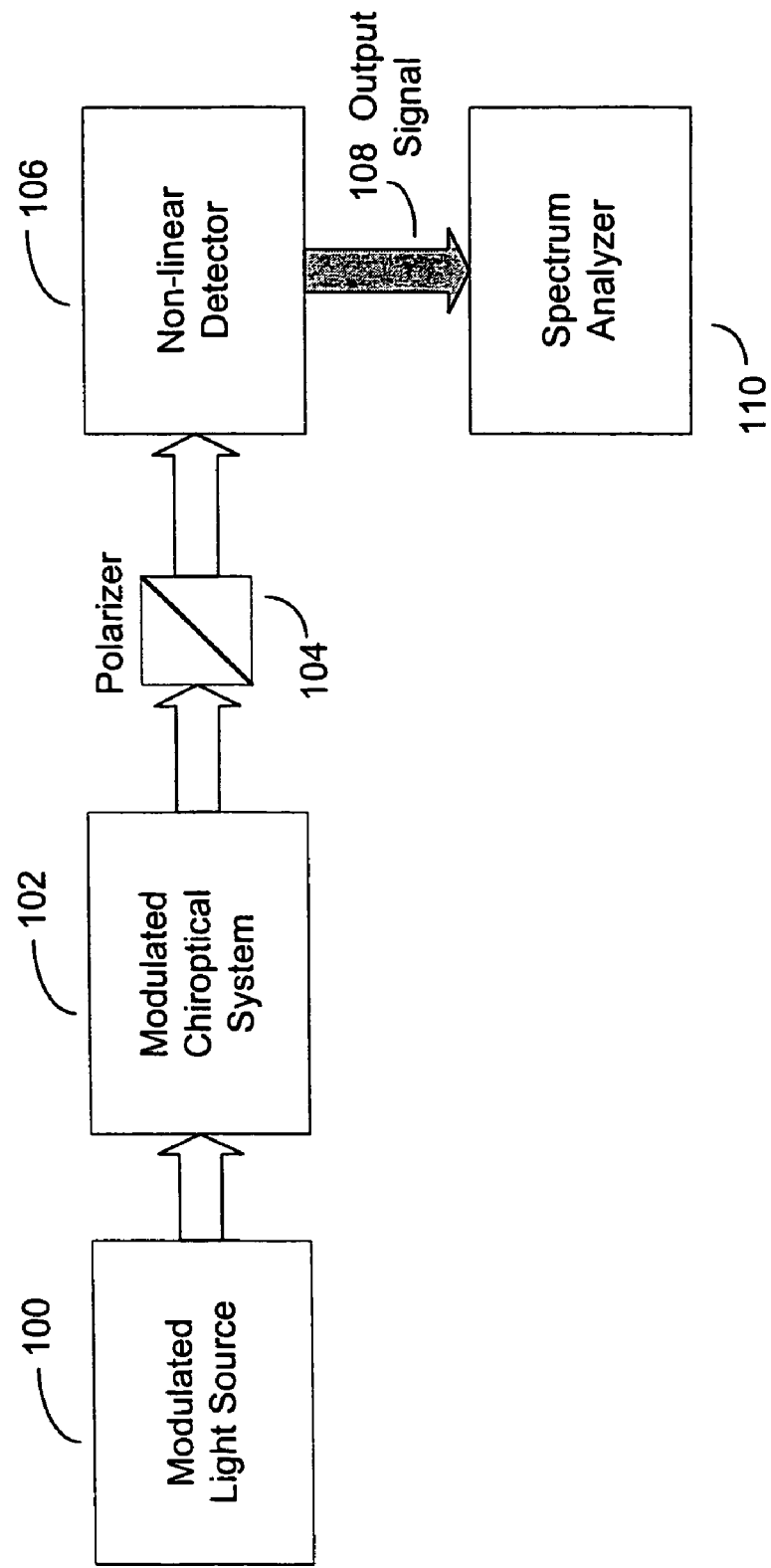
FIG. 1 is an exemplary block diagram of a chiroptical detection system in accordance with an embodiment of the present invention.

Referring now to FIG. 1, an exemplary chiral detection system has a light source 100, a chiroptical system 102, a polarizer 104, a detector 106, and a spectrum analyzer 110 as generally shown in FIG. 1. The light source 100 provides the probe into the system 102 for detecting a response at the detector 106. A high intensity monochromatic light source, such as a laser, is preferred as light source 100 but other types of light sources (e.g., a tungsten lamp, a xenon flash lamp, etc.) coupled with wavelength selectors (acousto-optical tunable filters, monochromators, etc.) would also work suitably as light source 100.

It is desired that the light from light source 100 is in a defined polarization state. This can be achieved by using a polarized laser or using a separate laser and input polarizer.

In the embodiment shown in FIG. 1, light source 100 is modulated. The modulation can be accomplished by modulating the light intensity, wavelength, or polarization state of the input beam probing the chiroptical system (i.e., $\omega$). The modulation is ideally a sine wave, but it is possible to use other types of modulation signals in other embodiments of the invention. For example, the light source 100 may be pulsed by a square wave modulation signal when the detector is inherently band limited to reject the unwanted higher order signals generated from the square wave signal's modulation spectrum. Thus, those skilled in the art will quickly appreciate that the selection of the type and rate of modulation will be an empirical choice selected by the system designer based upon parameters of the system's implementation.

The chiroptical system 102 is shown in FIG. 1 to be modulated as well. In one embodiment, the system 102 is modulated preferably using one of several known induced optical effects (i.e., magneto-optic [Faraday effect, Voigt effect, Cotton-Mouton effect], electro-optic [Kerr effect, Pockels effect] or photoelasticity to modulate system 102 directly at a frequency distinct from the modulated probe beam (i.e., $\phi$).

The transmitted light of the modulated probe beam exits a sample cell (not shown) within chiroptical system 102 and passes through an analyzing polarizer element 104 (e.g., a Nicol prism, a Glan-Laser polarizer, a Glan-Thompson polarizer, Glan-Foucault polarizer, Wollaston prism, Rochon prism, etc.). The transmitted light from polarizer 104 hits a non-linear detector 106, such as a photodetector (e.g., photodiode, avalanche photodiode, photo-multiplier tube, etc.) where the light is turned into an electronic signal 108. Those skilled in the art will appreciate that while a non-linear detector 106 is specifically mentioned in this example, other detectors, linear or nonlinear, that are capable of receiving and translating light from polarizer 104 into an electric signal may be utilized. The two modulation frequencies mix at the detector 106 and produce inter-modulated sidebands in the electronic output signal 108. The frequency spectrum of the output signal 108 may then be visually observed via a spectrum analyzer 110, which shows the observer the amplitude of different frequency related components (such as the level of signals at particular inter-modulated frequencies) making up signal 108. As will be discussed in more detail later, processing the output signal 108 can be accomplished with circuitry and logic other than spectrum analyzer 110, such as an analog-to-digital converter and a digital signal processor.

As discussed in commonly owned U.S. Provisional Patent Application Ser. No. 06/584,105, entitled "Systems and Methods for Chiroptical Heterodyning", observing chiroptical dependent signals at the inter-modulated sideband frequencies has several advantages in addition to the large gain imparted to the weak chiroptical signal at the fundamental frequency $\phi$. First, observation at the sideband frequencies allows one to avoid noise at either of the driving frequency fundamentals (i.e., $\omega$ and $\phi$), which tend to be noisy due to pickup in the system electronics. Secondly, whereas modern telecommunications routinely use super-heterodyning to down modulate high frequency signals for easier analysis (e.g., $\phi-\omega$), the additive sidebands in an embodiment of the present invention can also be utilized to obtain higher modulation rates than one could readily obtain in certain chiroptical systems (e.g., Faraday rotation). Therefore, these additive sidebands can further improve rejection of 1/f noise that typically plagues analytical measurements by allowing observation at higher frequencies via other techniques (e.g., lock-in detection, synchronous detection, double lock-in detector (such as that disclosed in commonly owned U.S. Provisional Patent Application Ser. No. 06/568,104, entitled "Double Reference Lock-in Detector")). In addition, direct modulation of the chiroptical system 102 is the preferred mode of utilizing lock-in analysis for signal recovery because the signals of interest (i.e., natural and induced optical activity) are directly modulated introducing less noise into the measured properties of interest.

There are several classes of chiral detection systems that may be used to implement embodiments of the present invention. The first type utilizes direct modulation of the input light amplitude coupled with another device to modulate a chiroptical property of the beam to probe a sample containing a chiral species. These systems represent a simpler modification to existing techniques of chiroptical analysis.

A second class of systems modulates the input light amplitude and directly modulates the chiroptical properties of the sample cell. In general, the direct modulation of the system of interest (in this case the sample chamber containing the chiral species) may be preferred as it may provide better or a more optimum noise rejection when detecting chiroptical properties of the analyte.

A third class of systems modulates a chiroptical property of the input probe beam (e.g., linear polarization state) and separately modulates a chiroptical property of the system containing the sample. These systems are preferred for the best noise rejection because these systems have the highest RMS optical power and maximize optical gain. Several examples of each of these types of systems are described with magneto-optic, electro-optic, acousto-optical, and photoelastic modulation.

Figure 2:
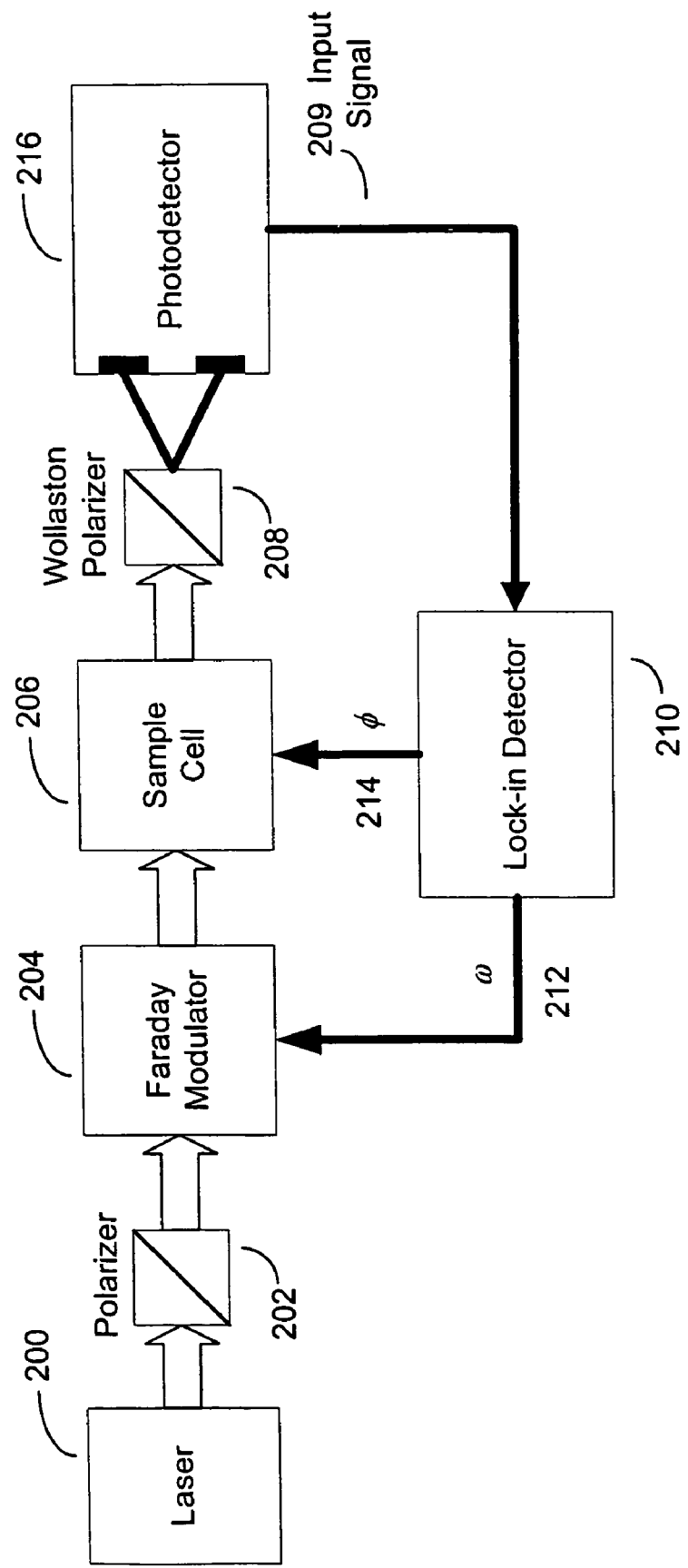
FIG. 2 is an exemplary diagram illustrating a prototype modified MOPED apparatus in accordance with an embodiment of the present invention.

Looking at these types or classes of chiral detection systems in more detail, FIG. 2 illustrates an example of an analytical instrument utilizing chiroptical heterodyning for chiral detection in accordance with one or more embodiments of the invention. This can be termed a modified Magneto-Optical Enantiomeric Detector or MOPED apparatus and is also disclosed in U.S. Provisional Patent Application Ser. No. 60/510,209. Referring now to FIG. 2, the example instrument includes a laser 200, input polarizer 202, modulator 204, sample cell 206, output polarizer 206 (also called an optical modulator) and photodetector 216 (shown implemented as a balanced photoreceiver). A lock-in-detector 210 is shown receiving an input signal 209 from the photodetector and providing signals 212, 214 as feedback modulating signals.

Optical Rail

Within the instrument, the optical elements of the system (e.g., laser 200 through photodetector 216) may be mounted on an optical rail to enable predetermined and stable placement of each optical element. In other words, use of an optical rail permits precision alignment of each optical element into a desired position relative to adjacent elements in the system. Depending upon the implementation, the non-optical elements in the system may or may not be mounted using the optical rail. For example, the lock-in-detector or other signal processing circuitry may be mounted separately in the system not utilizing the optical rail. Thus, any of the elements of the system may be mounted on the rail for ease of construction, placement, and enhanced reliability and operation of the system.

In one embodiment, a single optical rail is used. However, those skilled in the art will appreciate that alternative embodiments may use more than one optical rail to accommodate larger optical elements in a non-aligned configuration. In such non-aligned configurations, care is taken to provide the light beam from one end of the system to the other using flexible interfaces between optical elements, such as the use of optical fibers and the like. For elements that are non-optical, it will be appreciated that other ways of operatively coupling those elements within the system will be used. For example, the photodetectors and the lock-in detector may be operatively coupled using appropriate electrical wiring or cables.

In another embodiment, the optical rail may be designed on a picatinny rail. An example of such a picatinny rail is one implemented according to MIL-STD-1913, which is a published U.S. military standard for the alignment of optics. Some features of the optical mounting rail in this embodiment of the present invention may be similar to the mounting rail of MIL-STD-1913 in its basic construct of a groove dovetail feature that serves as the locking mechanism. However, the exemplary optical mounting rail in the embodiment may differ from the known mounting rail in significant ways.

Figure 3:
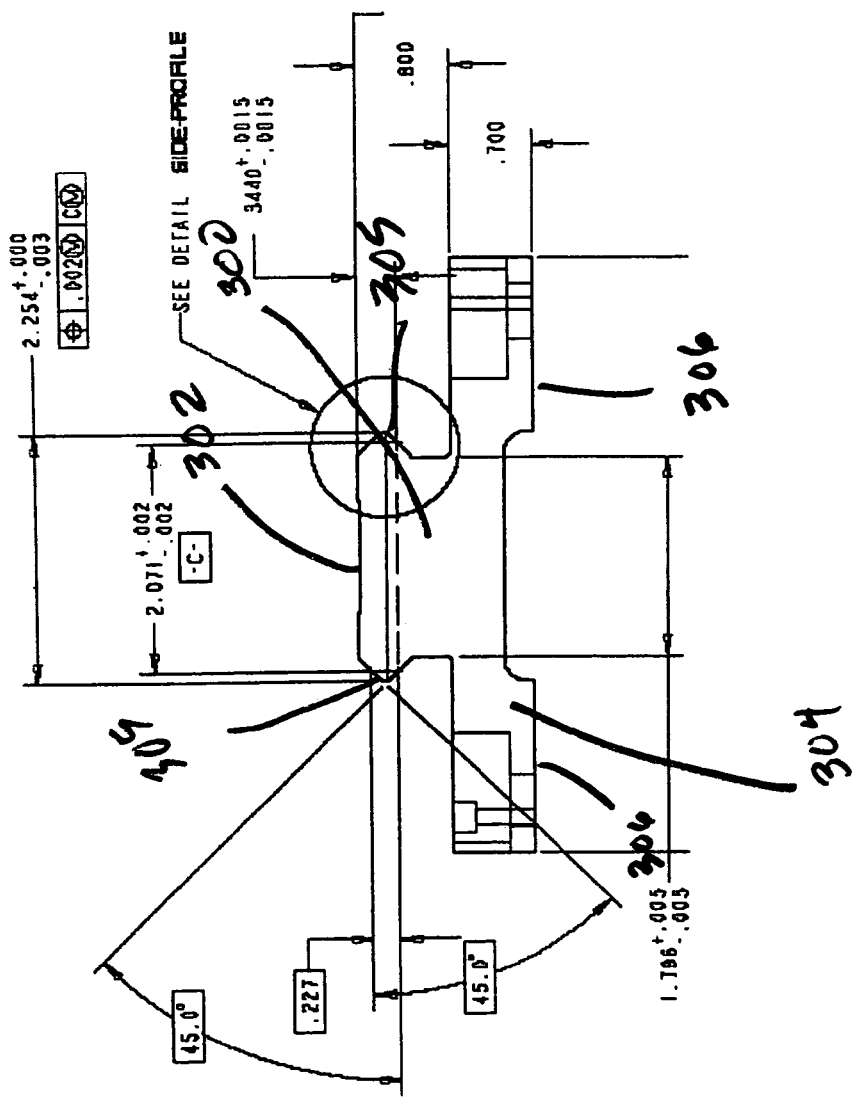
FIG. 3 is an exemplary cross-sectional diagram of an optical rail guide for use in accordance with an embodiment of the present invention.

In general, an exemplary optical mounting rail in an embodiment of the present invention may include a captive guide structure and a base portion that supports the upper captive guide structure as shown in FIG. 3. The captive guide structure 300 includes a top elevated platform 302 upon which the optical elements are secured. Those skilled in the art will appreciate that the angled The top elevated platform may be substantially wider and longer than its counterparts in the known mounting rail. This provides a much wider platform, which enables the optical elements to sit in a more secured and rugged fashion. Further, it reduces the possibilities of vibration, misalignment, and other problems that may affect the performance of the system. The wider platform is also easier to manufacture, ship, service, and install. In addition, the platform may be constructed of aluminum or other superior heat conductive material, In this way, the wider platform provides an enhanced surface contact with the optical elements and greater surface contact with the system's casing upon which the platform is mounted. In this configuration with such a wider platform, the optical rail advantageously serves as an enhanced heatsink for these optical elements. Specifically, the wider platform may rapidly conduct heat away from the optical elements during operation of the system.

To further improve stability and heat conductivity of the optical mounting rail, the base portion of the optical mounting rail may be significantly increased in width as compared to the known mounting rail and may be formed from aluminum or other heat conducting material. For example, as opposed to having a base portion that is similar in size to the top elevated platform as disclosed in MIL-STD-1913, the base portion of an optical mounting rail suitable for an embodiment of the present invention is extended out from the top elevated portion, such as double or more than double in width when compared to the already much wider elevated top platform. This substantial base portion further improves stability of the mounted optical elements and provides an even larger surface from which heat may be conducted away from these elements during operation. Additionally, the base portion of the optical mounting rail may be much thicker than the elevated top platform portion and, thereby, further enhance the stability of the optical mounting rail. The thicker base, when formed from aluminum or other heat conducting material, may additionally improve the optical mounting rail's ability to serve as a heatsink.

FIG. 3 is a diagram showing a cross-sectional view of an exemplary optical rail in an embodiment of the present invention. Referring to FIG. 3, the exemplary optical rail is shown with a captive guide structure 300 having an elevated top platform 302 of a substantial width. Two dove tail lips 305 protrude from the sides of the structure 300. The rail further includes a base portion 304 that extends out from the base of structure 300. In this embodiment, the elevated top platform 302 has a width of 2.071 inches, which is almost triple that of the Military published standard for mounting structures. Additionally, the corresponding base portion 304 in this embodiment is more than twice the width of the elevated top platform 302 at 5.350 inches. The base portion also shows a substantial thickness of 0.7 inches. Further, the embodiment of FIG. 3 illustrates bottom surfaces 306 of the base portion 304 that provide direct thermal contact with the casing on which the rail is mounted. Those skilled in the art will appreciate the enhanced stability and heatsink function that are provided by the above features.

Figure 16:
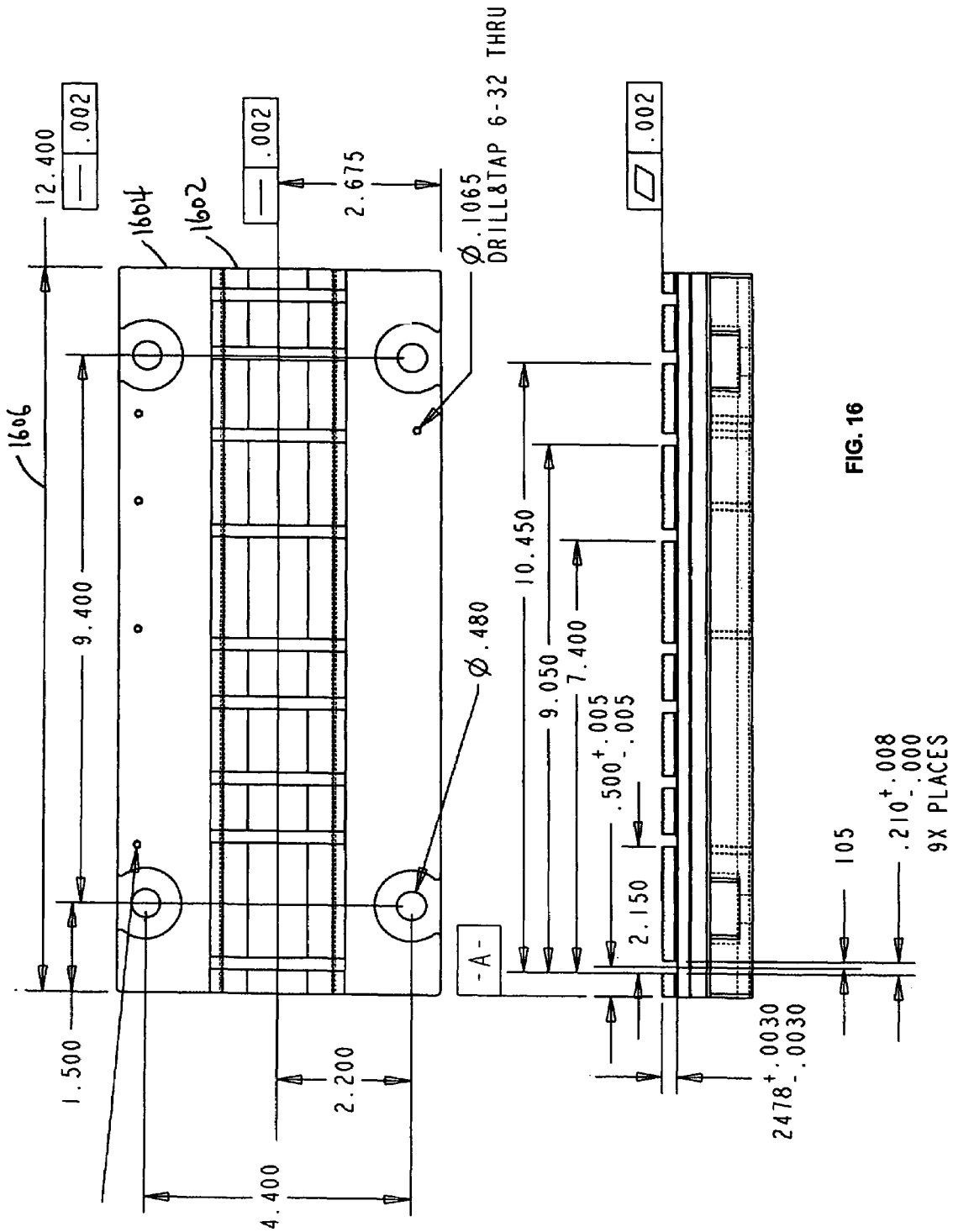
FIG. 16 shows exemplary top and length views of an optical rail guide for use in accordance with an embodiment of the present invention.

FIG. 16 shows exemplary top and length views of the above optical mounting rail of FIG. 3. In proportion to the significant width of both the elevated top platform 1602 and the base portion 1604, the length 1606 of the optical mounting rail is at a substantial 12.4 inches, which allows the optical elements to be spaced out when mounted.

Those skilled in the art will also appreciate that while specific dimensions are disclosed in connection with the above FIGS. 3 and 16, any other suitable mounting rails having different dimensions may be implemented without departing from the spirit of the present invention. As mentioned earlier and while not shown in FIG. 16, it is contemplated that the optical mounting rail may be implemented in multiple parts depending upon the system application and the physical limitation of dimensions within the casing of the system. As such, an embodiment of the present invention may include a system with multiple optical mounting rails. In this embodiment, the elements mounted to the different rails would be operatively coupled to each other, depending upon what element (e.g., the laser, the sample cell, the photodetector, the lock-in detector, etc.) are on the different rails. For example, if the laser was mounted on a separate optical rail than the rest of the system, an optical fiber may be used to operatively couple the laser and the light it produces to the rest of the system mounted on the separate rail. In this manner, the system may still be ruggedly and securely mounted within the system's casing, provide enhanced heatsinking abilities for those elements that generate significant heat while isolating other elements on other rails from such heat, but doing so in a more flexible manner that would allow for a more efficient use of space within the system's casing.

Laser

Referring back to FIG. 2, laser 200 generates a probe beam of light provided to the input polarizer 202. In an exemplary embodiment, laser 200 is implemented as a fiber laser operating at a wavelength of 658 nanometers. In a preferred embodiment, this allows the laser to deliver a high power Gaussian-shaped beam to the input polarizer 202 and remaining optical elements in the system.

Any light will suffice, but it is desirable to concentrate the light on the center. For example, a Gaussian beam is preferred in one embodiment where a small sample chamber volume may be desired. The majority of the power is in the center and is more likely to transverse the narrow bore flow chamber and the rest of the optics striking the photodiode. Any light striking the sides of the flow chamber tends to be depolarized upon reflection, thus introducing polarization noise (i.e., degrading overall linear polarization of beam). Thus, a Gaussian profile minimizes the amount of light closest to the walls. Other beam types, such as lines, are utilized in scanning applications and could work over shorter distances but would require photodiodes of a form factor to match the final beam profile and more difficult sample geometries.

The use of a fiber laser adds desired flexibility when mounting the laser within the system as it accommodates alternative instrument sizes and a position not aligned with the rest of the optical elements. Providing the light beam to the remaining optical elements may be facilitated with a fiber port assembly that focuses and locates the beam in its desired orientation. A micro-positioner can be used for such focusing and alignment functions. In an exemplary embodiment, an OFR FiberPort positioning device (described in U.S. Pat. No. 5,638,472) is an ultra-stable, miniature micropositioner, enabling active alignment of an AR-coated OFR aspheric lens for collimating or for free beam-to-fiber coupling.

Those skilled in the art will appreciate that principles of the present invention are applicable at wavelengths other than 658 nm. While other light sources with low noise characteristics at other wavelengths may be used for laser 200, light sources providing the light at 658 nm have been found to be advantageous due to low absorption characteristics and the commercial availability of modestly priced high power laser diodes (e.g., 30-70 mW). Further, single mode fiber can be used with the fiber laser, but those skilled in the art will appreciate that polarization maintaining fiber may be preferred for a few reasons. First, polarization maintaining fiber allows maximum light delivery to the rest of the system after the input polarizer. Polarization maintaining fiber is also less sensitive to vibration coupled noise, which would help achieve a less noisy output. Additionally, polarization maintaining fiber has improved fiber reliability requiring less care in fiber positioning and securing during system manufacturing, installation, and service.

Figure 12:
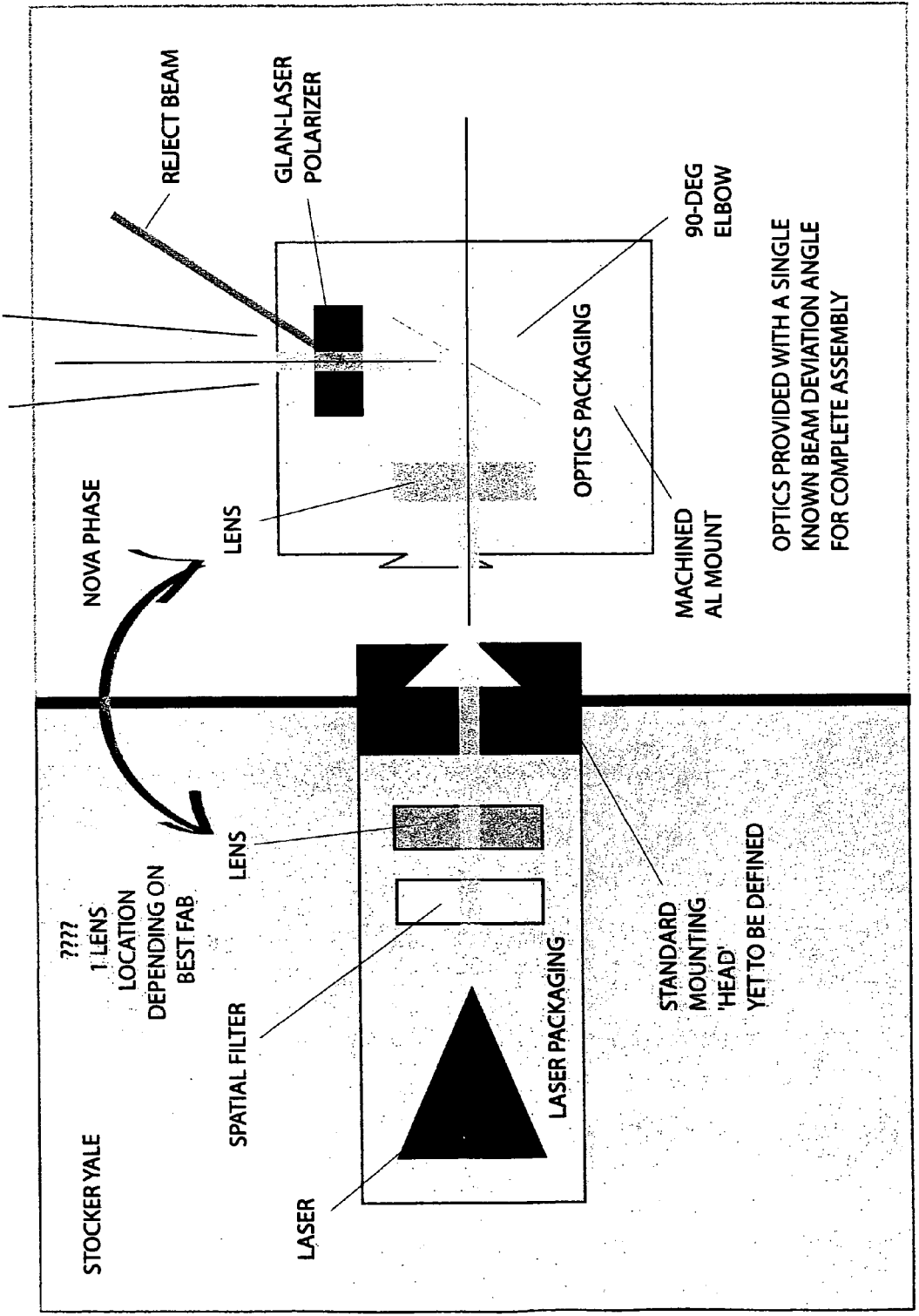
FIG. 12 is a diagram of an exemplary embodiment of the laser and optics packaging used within a chiroptical detection system in accordance with the principles of the present invention.

Another embodiment for producing an aligned Gaussian input beam is shown in FIG. 12. In this configuration, a laser containing a spatial filter and focusing lens is mechanically coupled to a steering optic (e.g., mirrored prism or dielectic coating for reflection at laser wavelength) and polarizer assembly. This configuration has several advantages over the fiber laser, fiberport, and input polarizer configuration. By replacing the fiber with a spatial filter, the coupling losses into the fiber (typically 66% for elliptical input and 50% for circularized input), avoid loss the loss of polarization with non-polarization maintaining fiber (typical diode laser gives 1:100 polarization output), and avoid power fluctuations resulting from vibrational noise on fiber (i.e. physically moving the fiber around changes the output power). The lens following the spatial filter allows the beam to be focused to a preferred point in the optical path (e.g., the middle of the flow cell or the midpoint of the optical path to the detectors). This ensures that the majority of the input light goes through the small flow cell without spreading out to a spot larger than final photodiode at the end of the optical path.

Figure 13:
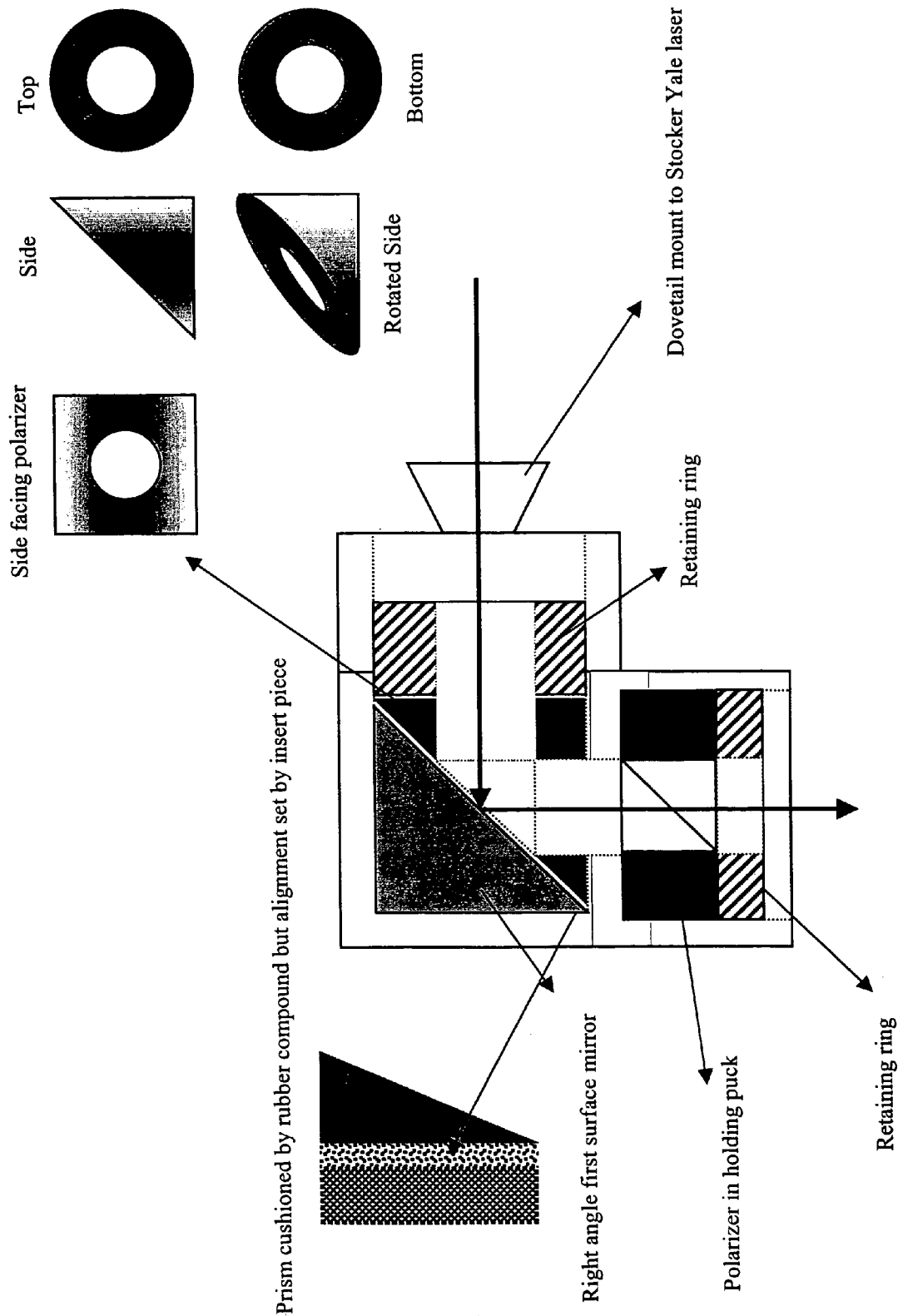
FIG. 13 is an additional diagram of the exemplary optics packaging from FIG. 12.

The beam into the steering optics package (see FIGS. 12 and 13) is typical offset at a slight angle from orthogonal to prevent back reflections into the laser. The 90° degree steering optic allows one to mount the laser onto the optical rail while minimizing the optical axis length. This allows a reduction of the expense of the optical rail as tight tolerances over longer distances (e.g., for precision optical alignment) are more difficult to machine. In addition, the proper choice of reflecting surface (e.g., dielectric coating for laser wavelength) can allow a small through beam for laser monitoring while reflecting the majority of the laser power (e.g., >99%) into the system.

After reflection, the input polarization is set by the output polarizer. Having the input polarizer as the last stage of the optical stack up is preferred since this ensures the highest quality beam into the chiroptical system (e.g., reflections or other optics all add some depolarization). The offset angle of the input polarizer can also be defined to a flat on the optics mount as opposed to providing a rotational adjustment. Having a single tolerance stack up is preferred from an alignment standpoint as one adjustment of the combined laser/optics package is needed to align the system (as opposed to multiple tweaks which takes time and is less robust).

Input Polarizer

Referring back to FIG. 2, the input linear polarization state of the light beam from laser 200 may be adjusted by the input polarizer 202 before it is provided to modulator 204. In exemplary embodiments of the present invention, the input polarizer 202 may be implemented with a polarizing crystal made of material, such as $YVO_4$, a-BBO or calcite. In another embodiment, the input polarizer is implemented as a glan-laser calcite crystal. The glan-laser calcite crystal works well in this role because it is commonly available and the reject beam is not used nor is an optical hazard as the crystal and overall unit are contained and shielded from direct eye access. The input polarizer may be part of laser 200 (see also FIG. 12) or may be implemented as a separate optical device.

Sample Modulator

Figure 4:
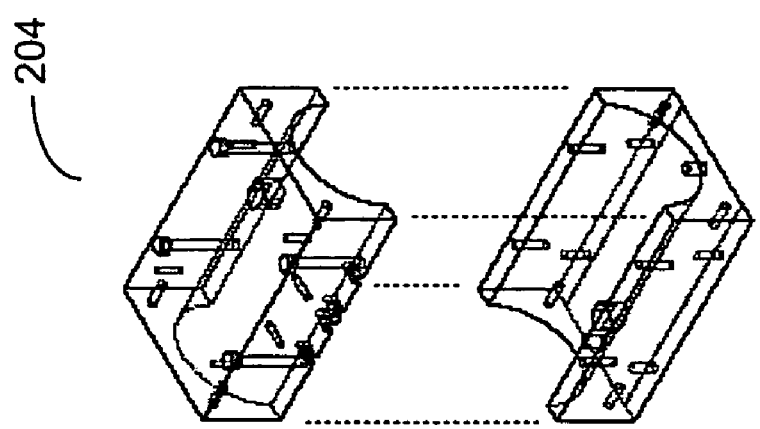
FIG. 4 is a perspective diagram showing an exemplary modulator in two parts in accordance with an embodiment of the present invention.

The optical modulator and the sample modulator are two distinct units both with low reluctance 430FR clamshells surrounding them. As illustrated in FIG. 2, sample modulator 206 receives the polarized light beam and imparts a modulation upon the sample by an AC modulating magnetic field parallel to the beam propagation (Faraday effect). The sample modulator 206 is modulated by signal 214 at a frequency of $\phi$. In another embodiment, the sample modulator is configured such that a low reluctance return path surrounds the sample modulator cell 206, as shown in FIG. 4. Referring now to FIG. 4, optical modulator 204 is shown as two outer shells in a clam shell configuration. The outer shells may be made from material that reduces eddy current losses, such as 430FR stainless steel. Those skilled in the art will appreciate that 430FR stainless steel is a readily machined soft magnetic ferritic steel with a relatively high volume resistivity. The outer shells may be machined into the two halves with a square outer profile that allows alignment matching to the optical rail and surface mounting of heat transfer pads. In this embodiment, the inner diameter of the modulator is precision machined to place the sample flow cell 206 along the center line of the optical access. Thus, the match of the inside diameter for the shell and the outer diameter of the interior sample flow cell controls the critical alignment of the sample flow cell 206 to the optical path and machining based on concentricity is preferred from a tolerance perspective. In this way, the outer shell conformally holds the sample flow cell in a desired position.

The outer shell of the sample modulator provides several notable and advantageous functions. First, the outer shell provides a flat surface to facilitate precision mounting to the optical rail. Additionally, the outer shell can provide a large thermal area and low thermal resistance to help dissipate heat generated in the modulator's coil (resistive losses). The outer shell in this configuration can also provide a low reluctance return path for the field enhancing the interior field being applied to the sample for the same applied current. Using this configuration also advantageously provides containment of the field to prevent undesired cross-talk between the two modulators (if the chiral detection system uses two modulators) and undesirable pickup in other chiroptical detection circuits (for those chiral detection systems that may use only a single modulator).

Furthermore, using a configuration of the sample modulator in two halves introduces a break for the circular eddy currents (laminations) further disrupting eddy current heating. More extensive laminations would also help address such eddy current issues, but require more complex machining (e.g., multiple plate stack up and binding), which is often costly.

Two coils, such as the coils shown as the hashed areas in FIGS. 6B and 6D, are utilized to reduce impedance at the applied frequency in addition to the use of a series resonant circuit. In one embodiment, the coils are implemented with Litz wire, which can also be utilized to reduce impedance at the desired driving frequencies. The skin effect and proximity effect contribute to coil losses. However, at certain frequencies and in multi-layer coils, the proximity effect can be the major contributor to coil losses (e.g., higher resistance to increasing AC modulation). Despite the added cost, reduction in impedance by utilizing Litz wire for AC modulation allows a single coil to be utilized with lower overall losses compared to two parallel coils of a single conductor in the same volume. Having one coil, using Litz wire, is preferred as the interior field is more uniform and heat associated with the impedance loss can be reduced to a point were passive cooling of the assembly is sufficient. In one embodiment, thinner wire may be used for the coils in connection with a bobbin. Due to the wire's thinness, the wire making up the coil may be wrapped around the bobbin in layers to achieve the desired effect. Use of passive cooling simplifies the system and removes the potential maintenance issues with a cooling fan.

Sample Flow Cell

The sample cell 206 (also called a flow cell or sample flow cell in some configurations) is a device that introduces the sample analyte, usually under flowing conditions, while being exposed to modulation. In the illustrated system of FIG. 2, the sample cell 206 is directly modulated by the sample modulator built into or integral with the flow cell in an analogous manner to (Faraday rotation) yielding modulated chiroptical signals dependent on the Verdet constant and natural optical activity of the sample modulated by signal 214 at a frequency of $\phi$. In another embodiment, the sample cell may be positioned within the outer shells of a low reluctance return path, such as the clam shells previously described as being made from 430 FR. As will be discussed later, an optical modulator may also be used in this configuration.

FIGS. 5A-E illustrate an exemplary sample flow cell for use in an embodiment of the present invention. Referring now to those figures, the sample cell 206 holds analytes dissolved in a solvent while the probe beam is applied through the sample cell (and analytes in the solvent) while additional modulation is applied to the probe beam. In one embodiment, the sample flow cell is designed to facilitate application of the magnetic field to an inner flow chamber designed for high performance liquid chromatography (HPLC) analytical flow conditions. In order to have good peak resolution for most analytical applications, the sample flow cell should have volumes less than approximately 50 micro-liters ($\mu$l). In this application, the material selected for the sample flow cell assembly should not interact with the applied magnetic field (e.g., eddy current heating or magnetic shielding effects). Those skilled in the art will appreciate that some embodiments of the present invention may use glass and plastics for sample flow cell materials, while a preferred plastic is Polyetheretherketone (PEEK) due to its desired chemical resistance, high melting point and relative ease with which it can be machined. Those skilled in the art will further appreciate that some other embodiments of the present invention use austenitic steels, such as stainless steels, which are nonmagnetic and are readily manufactured with precision tolerance. Such steels exhibit good heat transfer characteristics and low eddy current heating unlike aluminum. Additionally, the use of austenitic steels have further advantages in this application in that they may be used inside the applied field without affecting the magnetic fields influence on the sample.

Figure 5A:
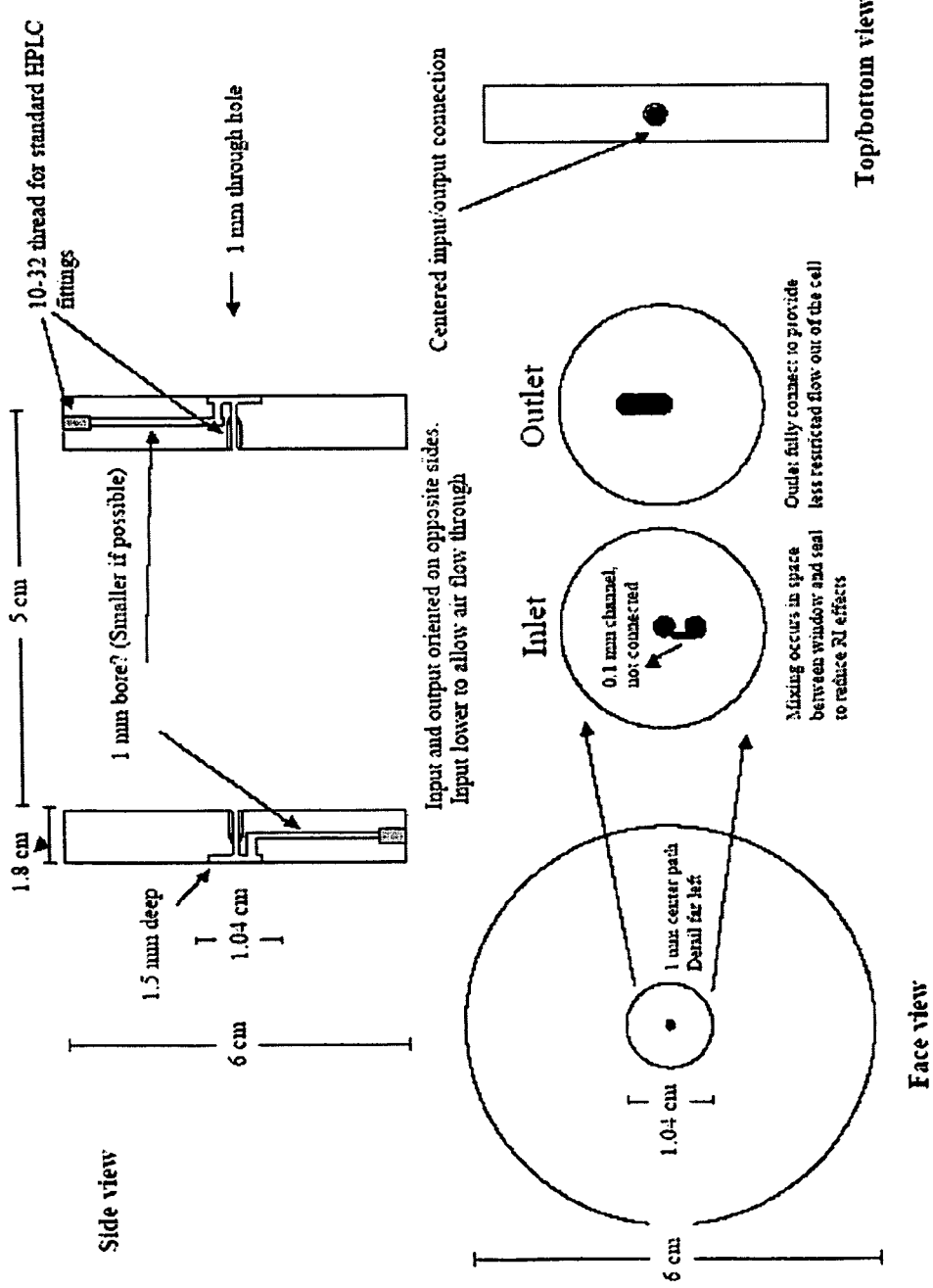
FIGS. 5A-5E are diagrams of embodiments of a sample flow cell in accordance with principles of the present invention.
Figure 5B:
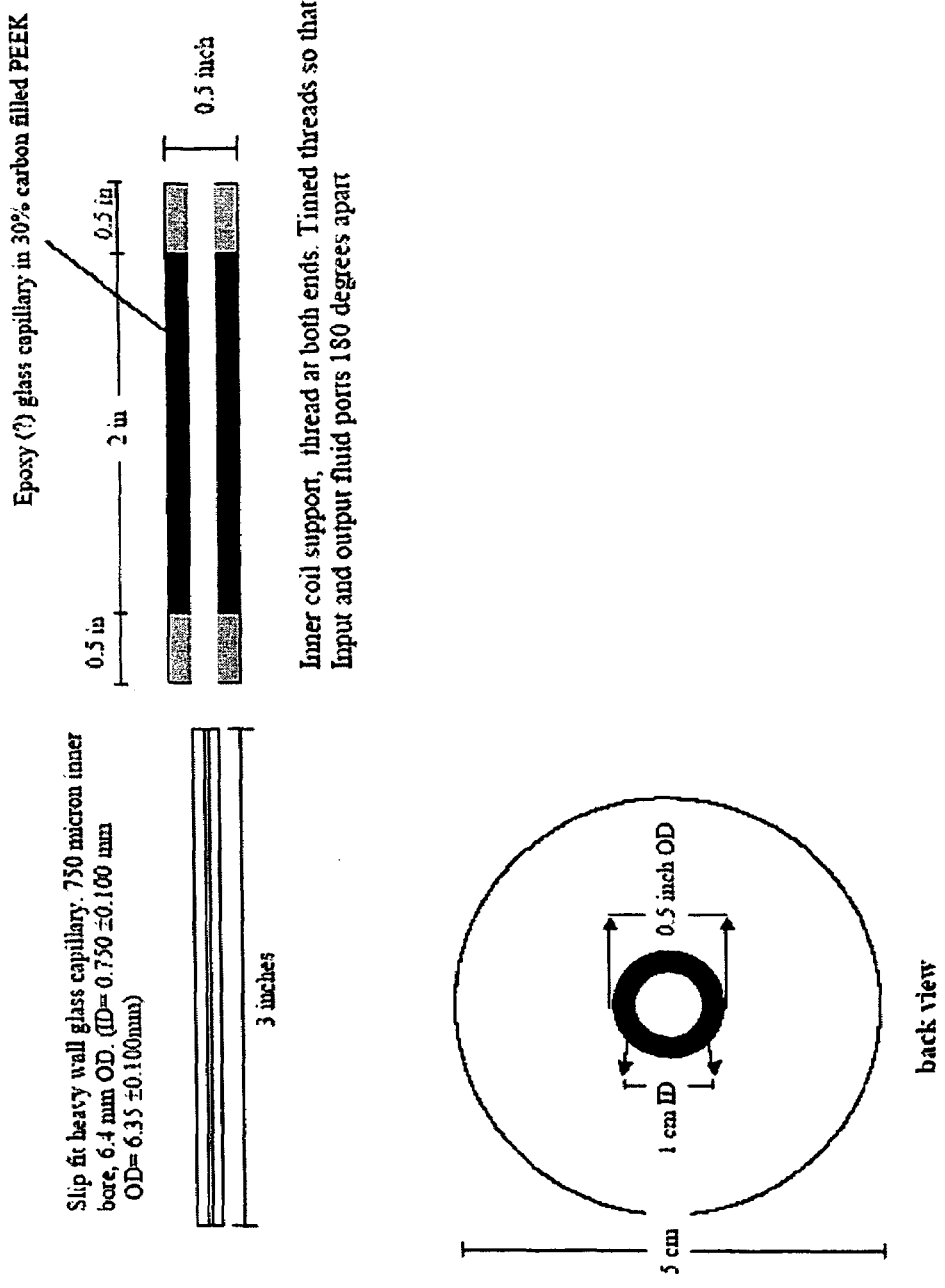

In one embodiment of the present invention, the sample flow cell uses two types of PEEK. As shown in the embodiments of FIGS. 5A & 5B, the ends of the bobbin utilize carbon filled PEEK since it is black (reduced reflections) and has an improved thermal coefficient (3× normal PEEK). The interior flow cell utilizes black PEEK with a thick walled glass capillary core. The thick walled glass capillary core provides a small flow chamber volume (e.g., approximately 750 micron diameter, but smaller sizes also available) while allowing for a much larger outer diameter, which is fixed (typically with epoxy) into a black PEEK. The large outer diameter of the glass capillary in this embodiment may be useful as machining or casting a larger interior bore for the black PEEK outer shell is much easier. The black PEEK outer shell may be needed for several reasons: the larger outer diameter (approximately 0.5 inches in this embodiment) matches the inner diameter of the copper coils or a bobbin inner core for Litz wire or other non-selfsupporting coil geometry. The outer diameter of PEEK can be machined with threads to fit the outer bobbin pieces (allowing sealed fit but access to putting on the coils), and the relatively low thermal conductivity of the glass and black PEEK shield the sample from excessive heating (i.e., outer OD thermal contact on the coil is much lower thermal resistance), and the black PEEK has a high electrical resistance. An alternative embodiment uses black PEEK for the whole assembly. The use of extruded tube black PEEK may also be desirable as black carbon fiber PEEK has to be cast, which may result in voids in the material. In yet another embodiment, black bearing grade PEEK is utilized since this material has best machinability of all the available PEEK materials.

Figure 5C:
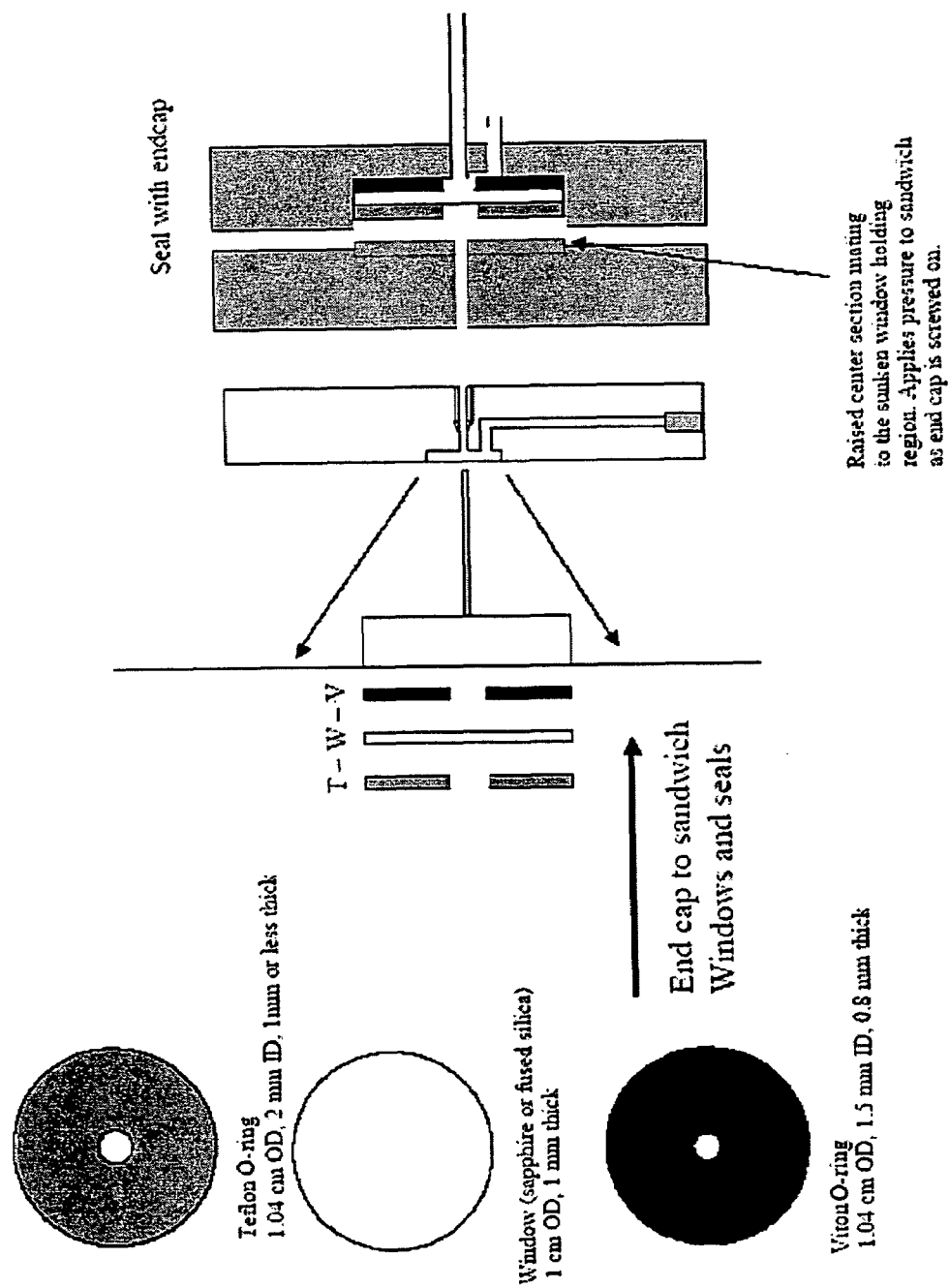
Figure 5D:
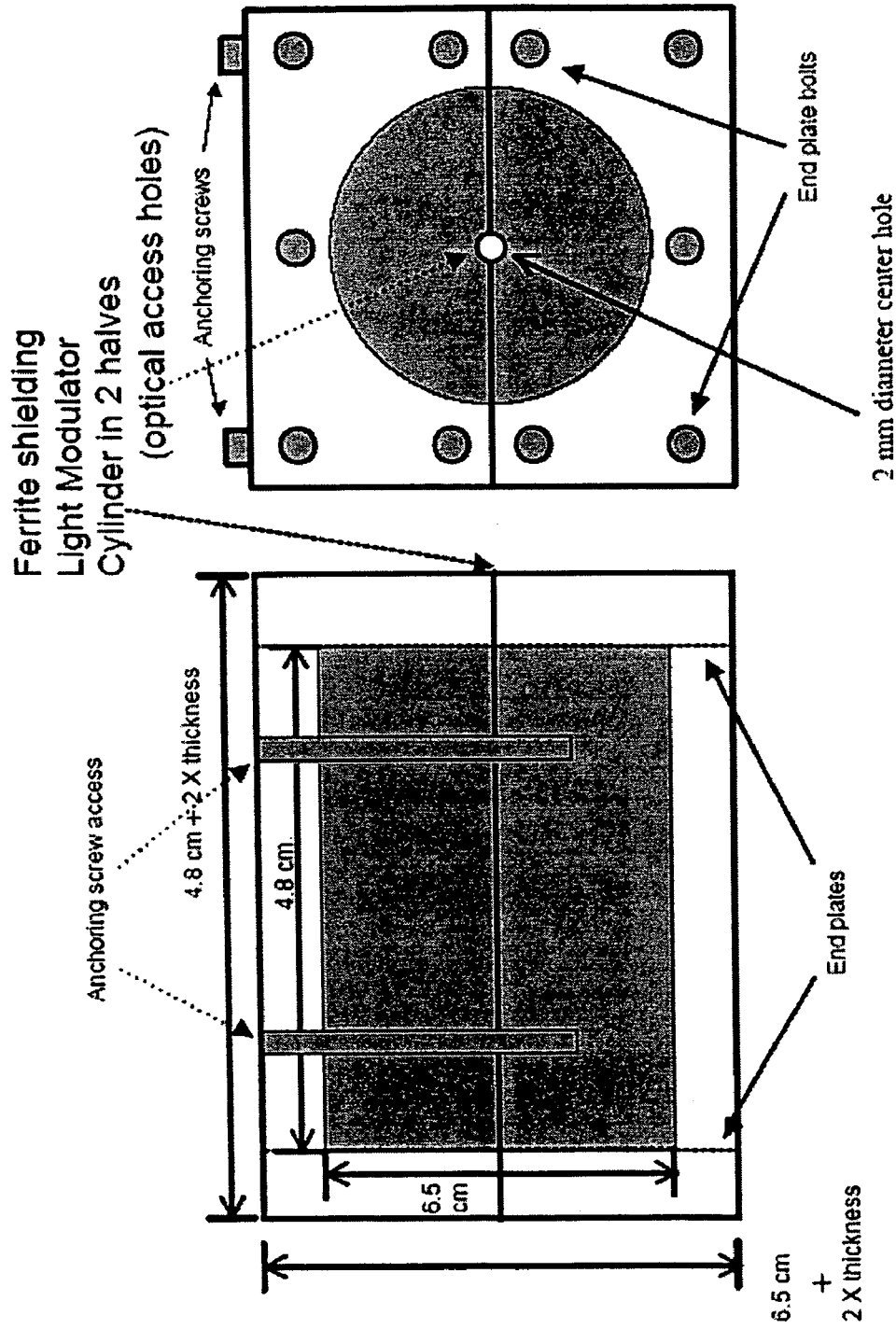
Figure 5E:
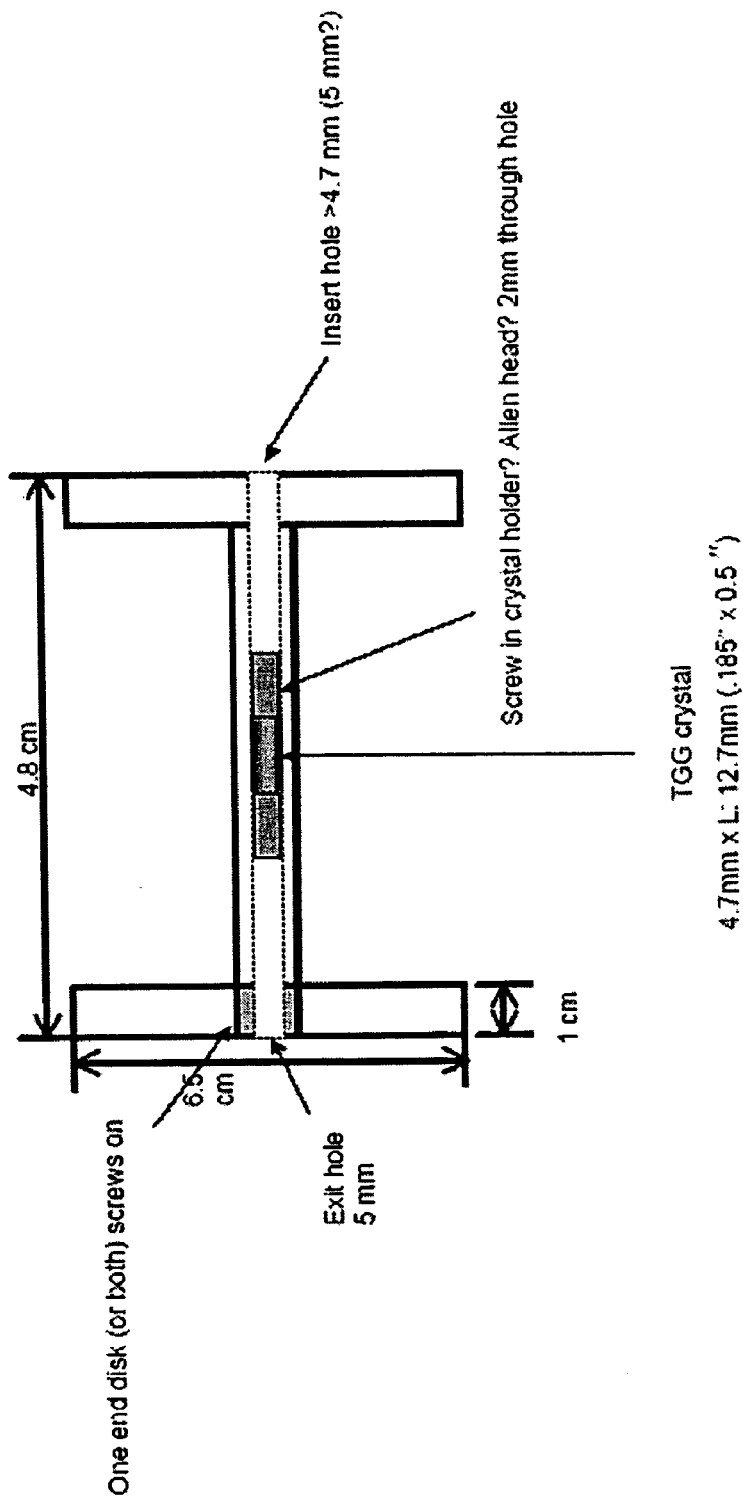

As shown in FIG. 5C, the outer bobbin halves allow the stack up of the optical window and seals. The stack up is arranged so as to give a good even seal (no local stress) when the outer cap is screwed down. In addition, the outer Teflon seal allows the rotation of the outer cap without apply torsional stress to the optical window or underlying Viton seal. The input chamber (shown in FIG. 5A) is also designed to facilitate rapid mixing under normal flow conditions thus minimizing RI effects due to solvent variation that could introduce noise. The PEEK tubing connector section of the bobbin halve is designed so as to give a flat surface for precision machining (flat reference) and sink the tubing connector below the outer diameter of the flow cell assembly giving more tolerance for variation as the input hole of the shell no longer needs to precisely match the connector location (PEEK tubing can bend).

As shown in FIG. 5A, the location of the input and exit connectors are bottom and top, respectively. This facilitates the removal of air bubbles, which often occur during setup and operation of HPLC systems. Those skilled in the art will appreciate that a trapped bubble would interfere with any sample analysis due to light scattering. In this embodiment, regular PEEK could also be used for the glass capillary outer shell in FIG. 5B especially in cases when a self supporting. Optical windows can also be from various materials (e.g., fused silica) but are antireflection coated for the operational wavelength (preferably narrow band).

Figure 6A:
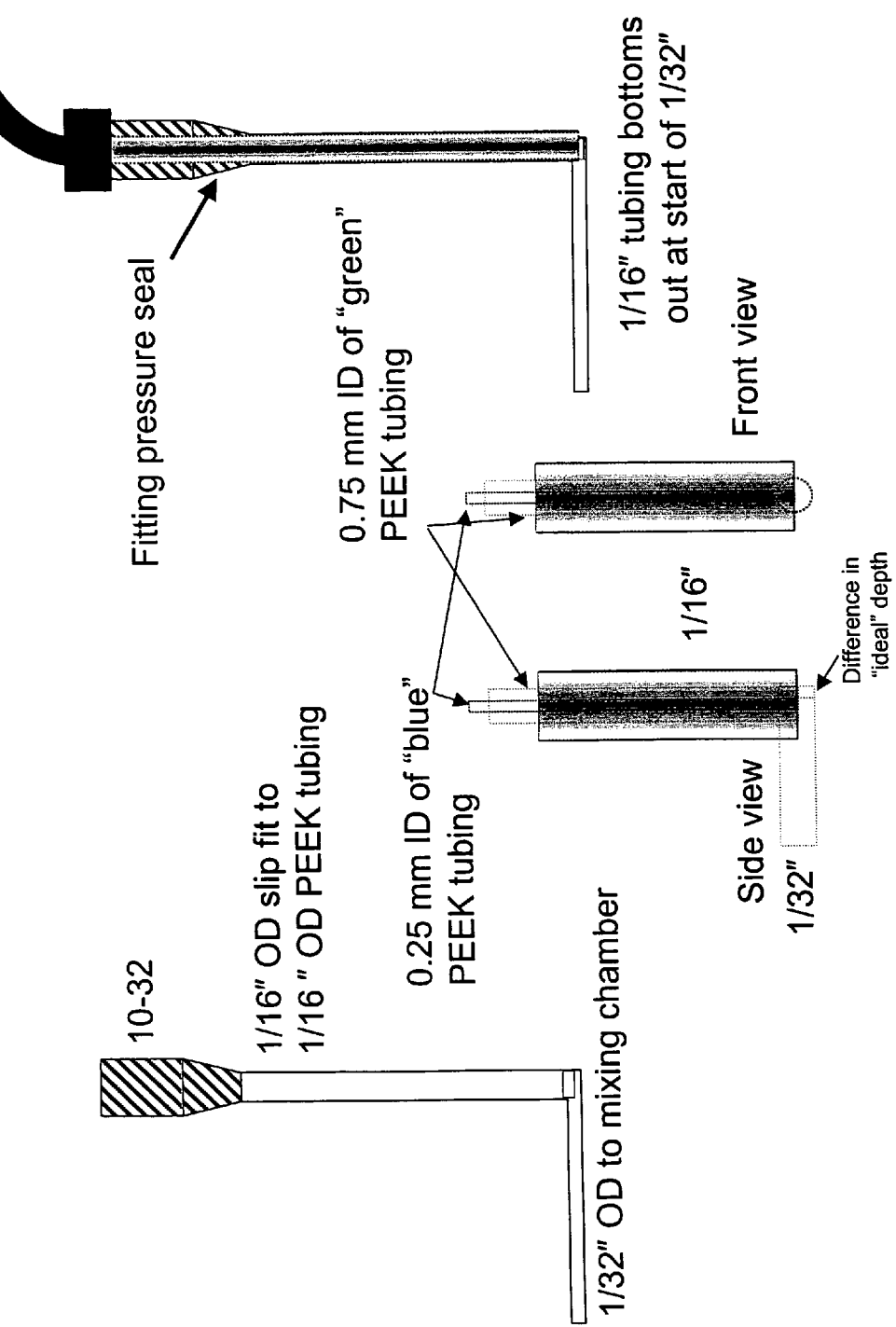

FIGS. 6A-C show details of another sample flow cell and the tubing fitting and flow for introducing the sample within the sample flow cell according to another embodiment of the present invention. FIG. 6D illustrates the top view and side view of an assembled sample flow cell bobbin with its coils shown as hashed areas. FIGS. 8A-E illustrate another embodiment of the sample flow cell's bobbin in accordance with the principles of the present invention.

Figure 7:
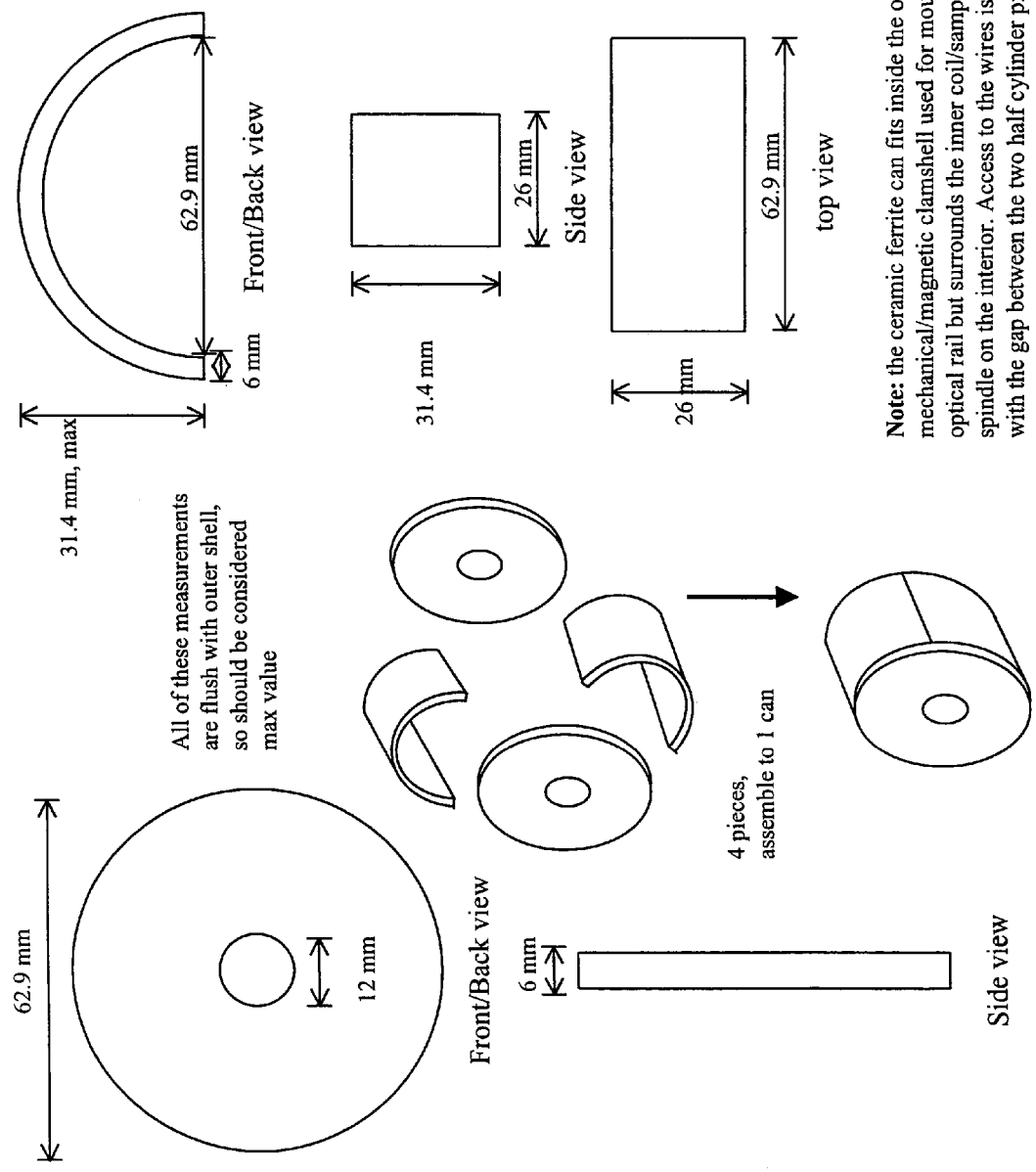
FIG. 7 is a series of diagrams for an exemplary mechanical/magnetic clamshell used to house the flow cell in accordance with an embodiment of the present invention.
Figure 8A:
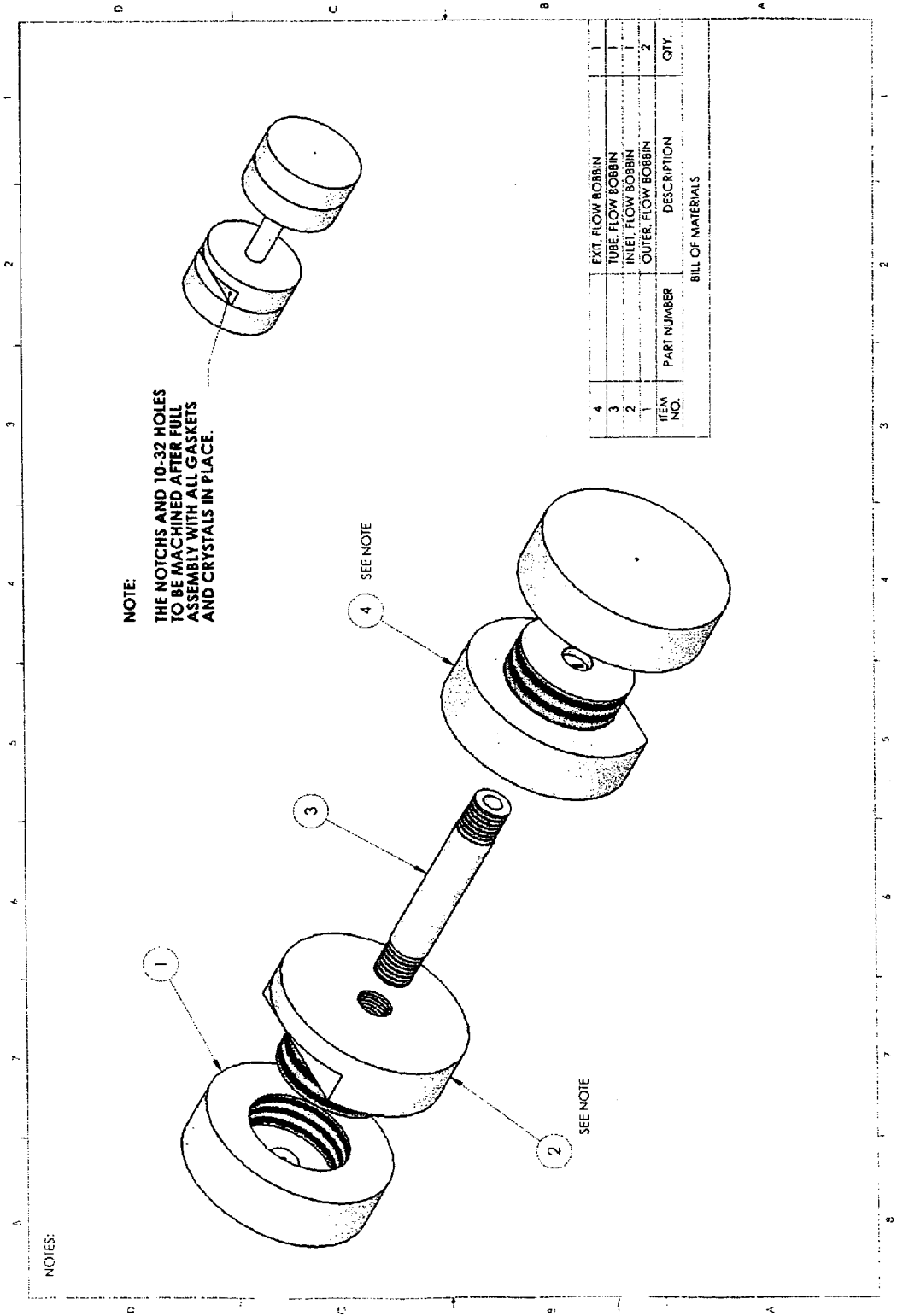
FIGS. 8A-8E are diagrams of additional embodiments of the sample flow cell in accordance with principles of the present invention.
Figure 8B:
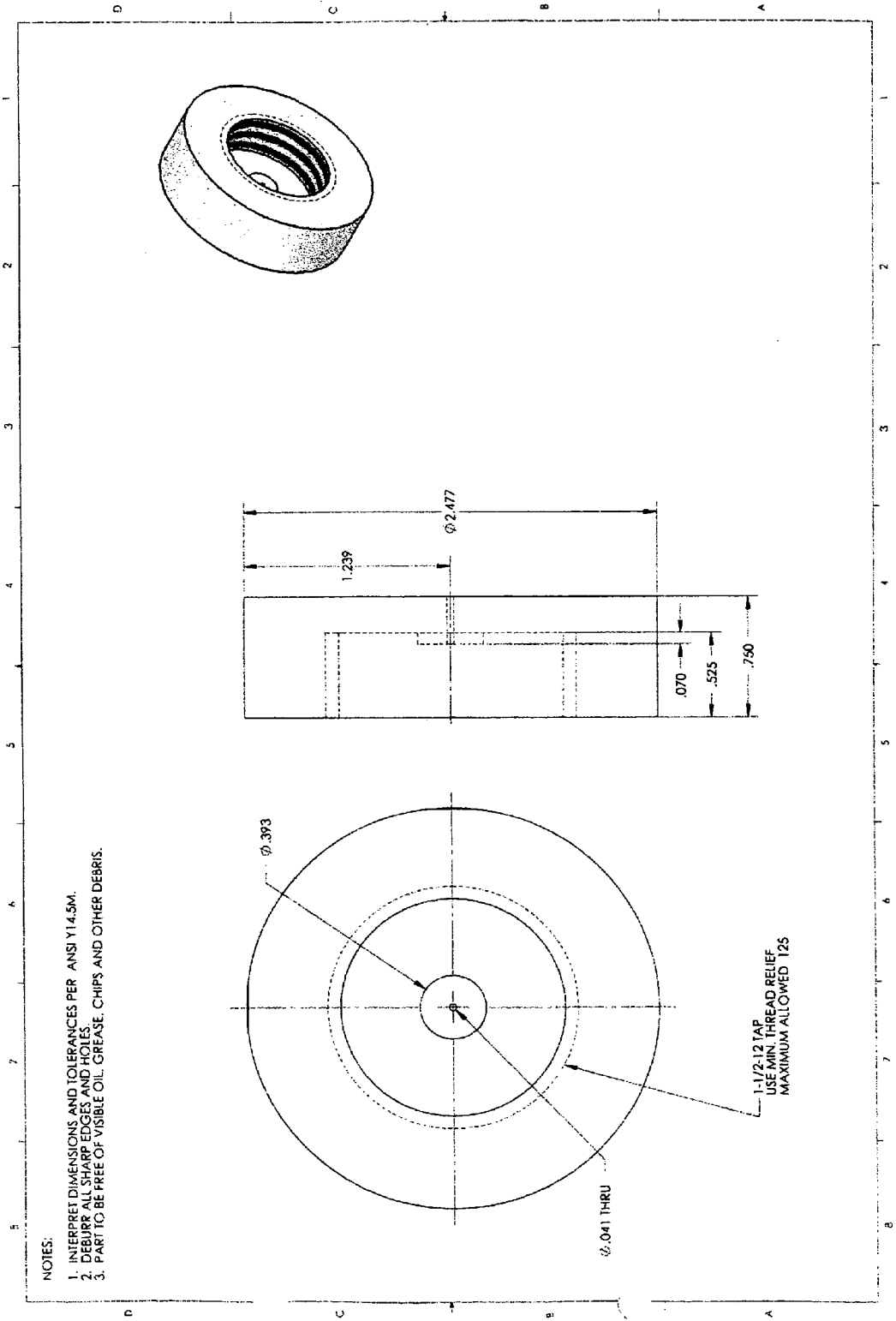
Figure 8C:
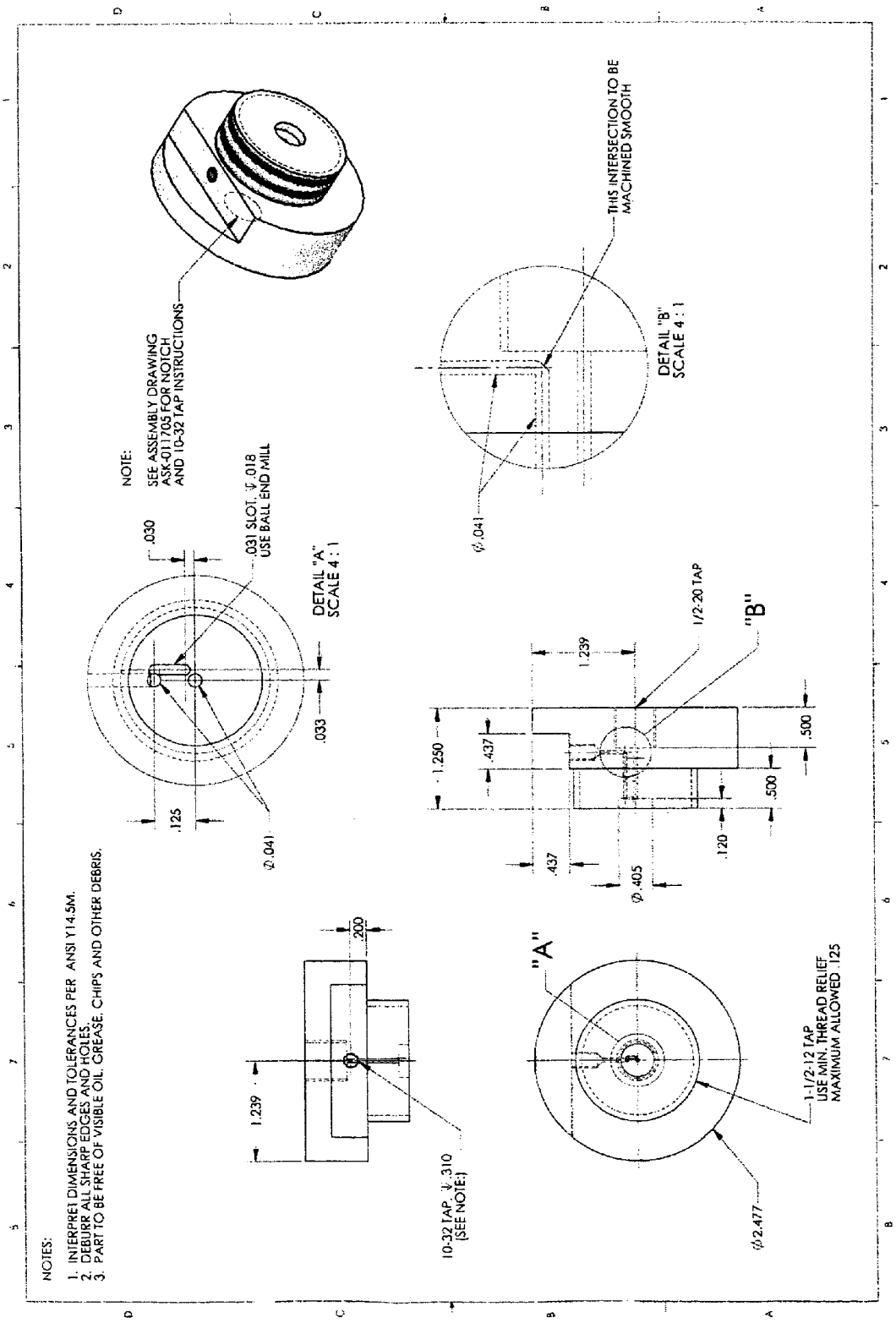
Figure 8D:
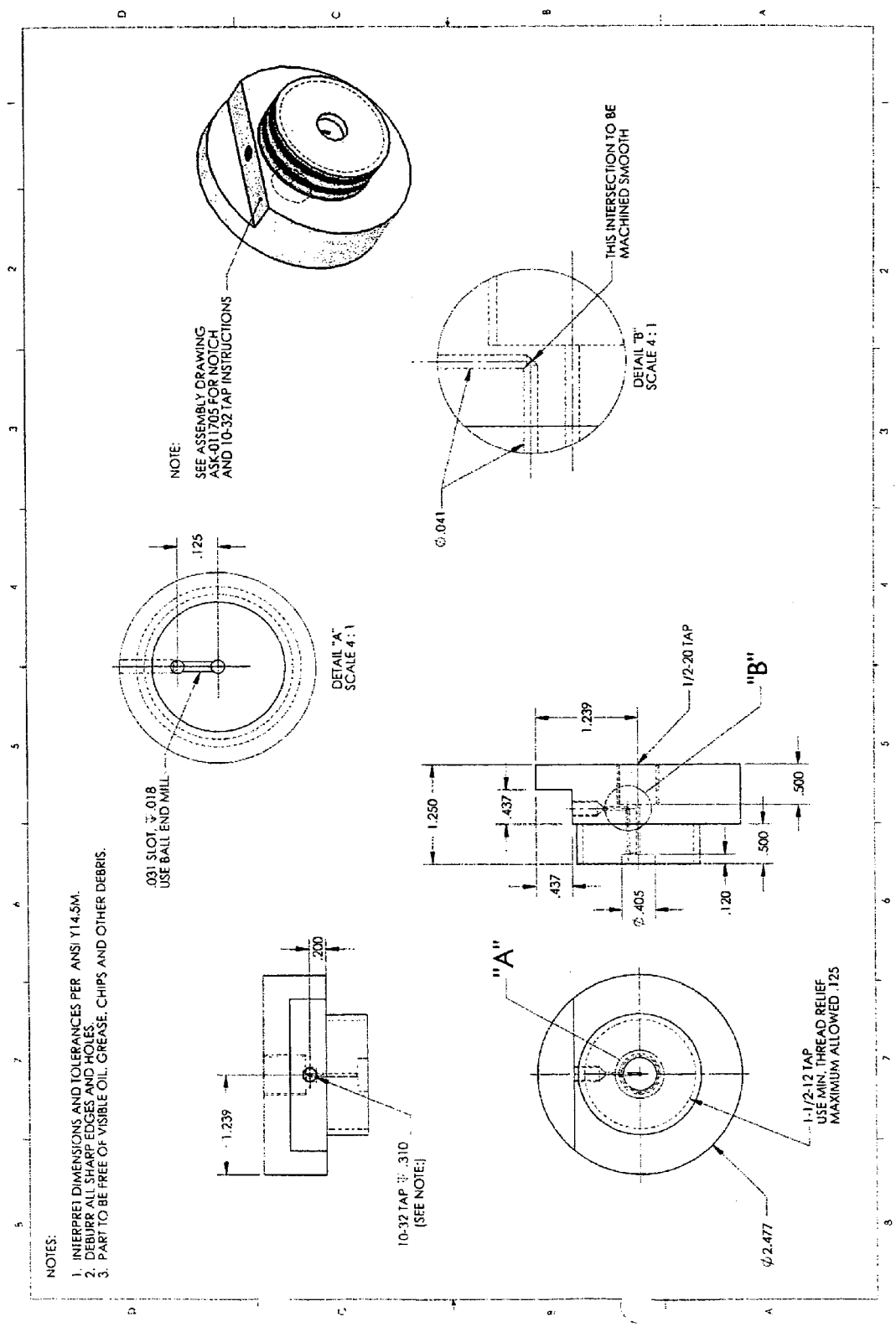
Figure 8E:
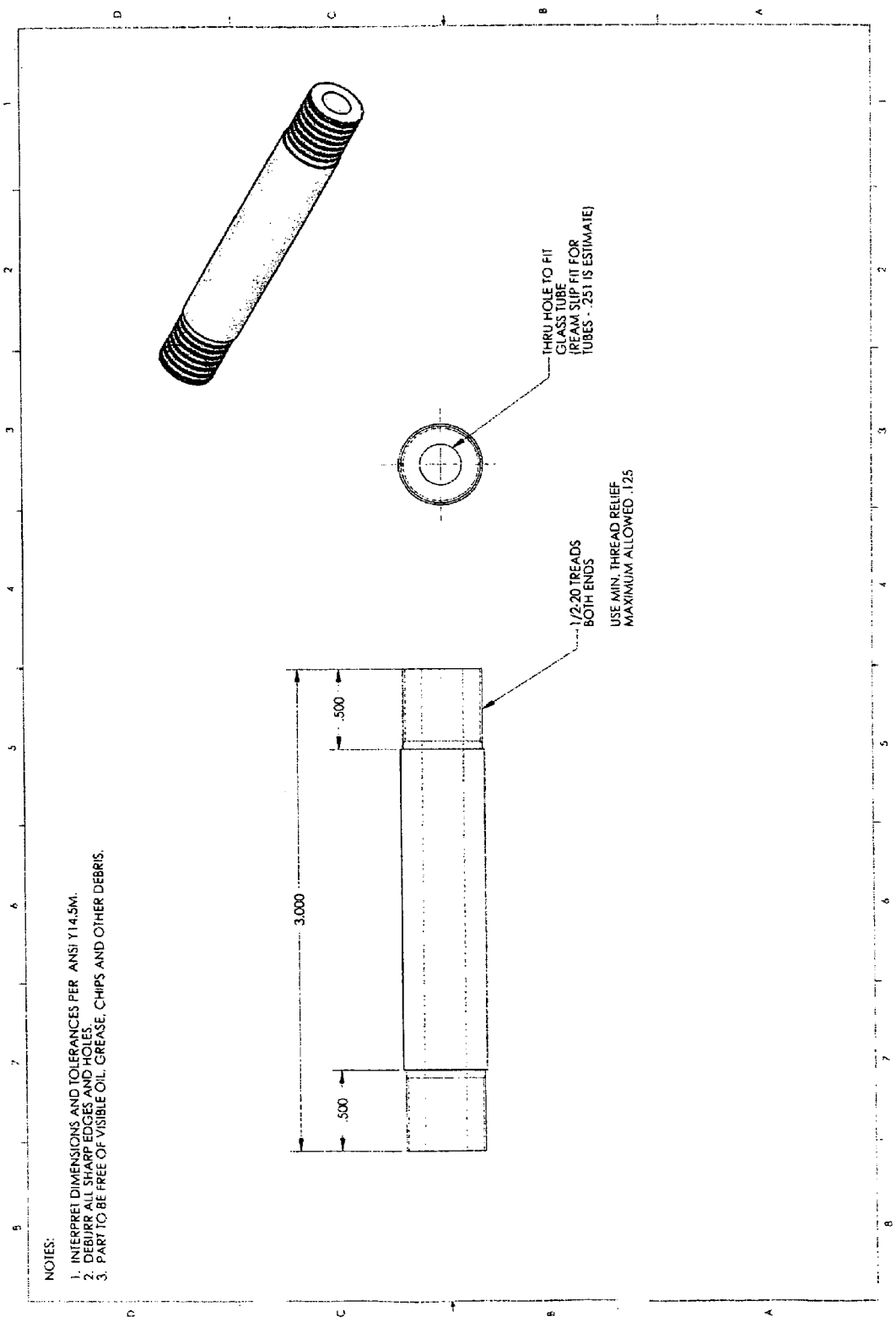

A ceramic ferrite can may be used to surround the inner coil/sample flow cell spindle on the interior of the clam shells as shown in FIG. 7. Such a ceramic ferrite can may be implemented in multiple pieces, such as the 4-pieces shown in FIG. 7. The ceramic ferrite can fits inside the outer mechanical/magnetic clam shell used for mounting the optical rail (e.g., the clam shell of FIG. 4).

Optical Modulator

As previously mentioned, the optical modulator 204 (implemented as a Faraday modulator in FIG. 2) receives the polarized light beam and imparts a modulation upon the beam. The modulator 204 is modulated by signal 212 at a frequency of $\omega$. In an alternative embodiment, the Faraday modulator 204 may be placed after the sample cell 206 instead of being before the sample cell 206. This is advantageous because the sample receives the highest quality focused beam and the acceptance window is less critical for the optical modulator. For example, a Terbium Gallium Garnet or TGG rod is approximately 5 mm in diameter. Accordingly, a 3 mm diameter window can be used to easily align with the narrow beam exiting the sample cell). In another embodiment, modulator 204 may be eliminated and the polarized light beam may be controlled or modulated directly to vary the intensity of the input light to the sample cell 206.

Referring back to FIG. 2, the exemplary optical modulator 204 includes the TGG rod held in a PEEK bobbin (see FIG. 5E) that imparts a second modulation onto the light beam. In one embodiment of the present invention, the optical modulator is surrounded by a shell with identical benefits described for the sample modulator. In addition this unit is made with similar specifications (e.g., length, ID, etc.) to facilitate less expensive machining cost. In addition, those skilled in the art will appreciate that there is a trade off between a higher applied field and a longer Verdet modulator (such as TGG but other crystals, such as Terbium Scandium Aluminium Garnet (TSAG) or high Verdet liquids, could also work) to achieve the same linear polarization modulation. In this case, the longer crystal is preferable from a thermal perspective inside the chiral detection instrument. The inner bobbin may be made from carbon filled PEEK on the end bobbin disk (outer diameter sets optical alignment) and the inner bobbin connector may be made from black PEEK to help address high temp stability, ease with which it can be machined, and absorption of stray light. A large optical acceptance (e.g., approximately 4 to 5 mm ensuring that the most critical alignment is the sample cell) and antireflection coating are desired.

In another embodiment, the optical modulator may be located on the optical rail after the sample modulator to ensure the most critical alignment receives the highest quality beam. PEEK set screws may position the Verdet crystal on the interior of the solenoid(s) for the most uniform magnetic field. Two coils are utilized to reduce impedance at the applied frequency in addition to the use of a series resonant circuit. In this manner, both the optical modulator and sample modulator are driven with series resonance, which provides a minimum impedance at the resonance frequency.

Analyzing Polarizer

Analyzing polarizer 208 receives the resulting probe beam from the sample cell 206, but is not a focusing lens or other optical focusing element. Instead, polarizer 208 splits up the beam into two diverging parts. In one embodiment, the analyzing polarizer 208 is implemented with a Wollaston polarizer, which yields two inversely coupled signal beams orthogonal to each other. Furthermore, the system in that embodiment further includes a spacing, holder, and detector designed to accommodate Wollaston polarizers made of $YVO_4$, a-BBO, or calcite (a less expensive material than $YVO_4$ with a large acceptance angle).

In this embodiment, the beams come out of polarizer 208 and illuminates two photodetectors placed in front of the beams within a balanced photoreceiver 216. Observing these two beams using the photodetectors in photo-receiver 216 yields a square law detector with a high common-mode rejection ratio (CMRR). In the illustrated embodiment, the driving frequencies $\phi$ and $\omega$ are synchronized with the lock-in internal reference, such as a voltage controlled oscillator (not shown) or a signal synthesizer (not shown) within lock-in detector 210, for accurate phase determination on the sidebands.

When the analyzing polarizer 208 is set so that one beam is at null relative to the input polarization, those skilled in the art will appreciate that the analysis of the resulting inter-modulated signals yields frequencies that are linearly dependent on the Verdet constant of the sample (i.e., $\phi+\omega$) and frequencies that are linearly dependent on the natural optical activity a (i.e., $\phi+2\omega$). Both of these types of signals provide useful analytical information to the researcher. When the analyzer is set so that one beam is at 45° relative to the input polarization, analysis of the resulting inter-modulated signals still yields frequencies that are dependent on the Verdet constant and on of the natural optical activity, $\alpha$, of the sample but the relation is reversed (i.e., $\phi+2\omega$ is now linearly dependent on Verdet).

In one embodiment, when the input light is modulated and the sample is modulated and observed at 45° for maximum CMRR (light modulation is common mode), the $\phi+\omega$ is linearly dependent on Verdet and the $2\phi+\omega$ is linearly dependent on optical activity (when $\omega$ is laser modulation and $\phi$ is sample modulation), which is reversed at 90°. Additionally, using 45° in an embodiment of the present invention may be desired as the observation point due to the superior common noise rejection of the large laser modulation component.

An exemplary mode of operation is to operate with one of the sample beams set to null relative to the input polarizer. Under these conditions, the fundamental frequency contributions to the signal output (i.e., $\omega$ and $\phi$ in the example of FIG. 2) from the photoreceiver 216 disappear and any harmonic distortion on the modulator coils in the sample cell 206 is advantageously eliminated from contributing to the detector output signal. Thus, the relatively large optical modulation is removed as the predominant signal in the output signal leaving the second harmonic of the optical modulation as the dominant signal in the output signal's frequency spectrum. This signal can be utilized to normalize the influence of light intensity fluctuations on other signals of interest.

Of the inter-modulation signals available at the null polarizer angle, both additive sidebands ($\phi+\omega$ and $\phi+2\omega$) and subtractive sidebands ($\phi-\omega$ and $\phi-2\omega$) may be utilized. While the additive sidebands may have a higher modulation rate than the subtractive sidebands, the subtractive sidebands may be preferred in some embodiments as they are associated with a higher gain at the transimpedance stage of the optical detector, which has a low pass filter topology. An additional benefit of the modified chiroptical detection system shown in FIG. 2, is that no moving parts are required. Absorptive centers are not necessary for the manifestation of Verdet or natural optical activity, so this technique is broadly applicable to chemical species previously difficult for conventional techniques (e.g., carbohydrates, weak optical activity, low ee %, high ee contaminants >99.5 ee %).

One potential complication for accurate observation of small changes in Verdet signals due to a chemical species of interest can be the relatively large background from the solvent. This large background signal can be removed prior to the lock-in analysis of the signal due to the analyte by a process analogous to active noise cancellation and this process is subject of a separate U.S. Provisional Patent Application No. 06/584,232 entitled "Systems and Methods for Enhanced Optical Detection using Active Single Frequency Nulling." Thus, at the null setting, a new parameter $\phi'+\omega'$ is utilized for changes in the Verdet constant relative to the solvent, where the contribution from the solvent is effectively zeroed. Therefore, the ratio of $(\phi+2\omega/\phi'+\omega')\times$(phase of $\phi+2\omega$) is linearly related to changes in the ee % of the sample because the optically dependent signal ($\phi+2\omega$) is normalized for concentration changes ($\phi'+\omega'$).

This ratio is an intrinsic property and independent of light intensity fluctuations from the light source since both signals, $\phi+2\omega$ and $\phi'+\omega'$, are linearly dependent on light intensity. As the ratio is an intrinsic property, samples can be compared for relative ee % purity in the absence of external standards. The ratio of $(\phi'+\omega'/2\omega)\times$(phase of $\phi'+\omega'$) is linearly related to changes in the Verdet constant of the sample relative to the solvent and independent of light intensity fluctuations from the light source. Thus, the Verdet constant measurement can be utilized to track concentration but the researcher also advantageously obtains the additional information of the analyte's Verdet constant relative to the carrier fluid giving additional specificity over a simply concentration measure.

DC Null Adjust Module

For more precise measurements, the exemplary optical assembly of elements in a chiral detection system can be operated at the null point of the input and analyzing polarizer. This eliminates the fundamentals from the two driving frequencies. As manual alignment of the input and analyzing polarizers is subject to error and polarization due to sample windows and optical components make change over time or during operation, an embodiment of the present invention uses a smaller Verdet crystal (implemented as a DC nulling device) added to the optical path to null the system via a feedback loop looking at the $f+2\omega$ (optical sideband) signal. Typically, this crystal is positioned after the optical modulator but before the Wollaston output polarizer, as the last device in the optical path. An example of such a system using an exemplary DC nulling device is illustrated in FIGS. 10 and 11A-H.

In an embodiment of the invention, this provides a precise adjustment because the constant current board controlling the DC field has 16-bit accuracy and is contained in the shield housing. This provides approximately 30 microdegrees of resolution for adjustment. By looking at the sideband, the DC null adjust can more precisely find the null point than previous Faraday feedback loop adjustments (see prior art patent GB2286244 for example). Furthermore, it is anticipated that such a DC null adjustment can be implemented in conjunction with manual nulling type adjustment aspects of the polarizers during instrument setup (e.g., fine tune after a manual adjustment). In addition, as the seek can occur very fast in an automated system, the instrument can include this adjustment as a regular part of the auto zero procedure or a less frequent systems startup diagnostic.

In additional embodiments of the present invention where the light beam is intensity modulated, the DC null adjust may be used to set the 45° operation point by minimizing the $2\phi+\omega$ signal. Also, in an exemplary embodiment of the DC null adjust device, the current source is one sided (e.g., 0 to 400 milliamps) and not bipolar (e.g., ±current). This requires an initial offset in the optical system (e.g., −0.5 degrees if the current adjustment adds positive rotation) so that approximately 50% of the DC null adjust current range will put the system into null (or 45 degrees for the laser intensity modulated system). This allows a simplified and more accurate circuit because it works at the midpoint of operation rather than close to 0 or the max output.

DC Null Adjust Feedback Loop

In another embodiment of the invention, the DC adjust coil can be used in an active feedback loop to maintain the system at null or the 45 degree balance point. The active feedback compensates for drift in the system and improves accuracy by reducing noise due to short term fluctuations and long-term baseline drift. In this embodiment, the highly accurate phase determination from the sideband mixing signals allows more effective feedback than previous schemes. In addition to less noise on the sideband signals used for feedback control, the DC adjust utilizes a highly accurate constant current source to provide the optical feedback to the system polarization. This current source is preferably a high bit low noise system set to cover the maximum adjustment range necessary for the feedback loop. In one exemplary embodiment, a 16-bit or 24-bit constant current source interfaced with a DSP allows adjustment over a 1 degree or smaller range using a TGG crystal in a DC coil. A smaller optical rotation range, such as 200 millidegrees, allows finer feedback control as the bit resolution is increased but the capability of the system to compensate for larger drifts is reduced. Thus, the range is a trade-off between resolution and total range necessary to compensate for the largest drift expected in the system.

Thermal Contacting with the DC Adjust Coil

One source of noise observed in the system was attributed to thermal variations in the Verdet constant of the TGG crystal utilized in the DC adjust coil. The driving circuitry was designed as a constant current source to remove thermal variations from influencing the applied magnetic field but the TGG crystal was not immune to temperature effects. A method for reducing the contributions of these thermal variations is to thermally contact the DC coil to the larger thermal mass of the magnetic shield surrounding the coil and providing mechanical coupling to the optical rail. In this manner, the larger thermal mass of the outer shield effectively dampens short-term variations in coil temperature. In addition, running the coil with a constant offset current (e.g., null or balance point at midpoint off current range) advantageously reduces the influence of external temperature variations on the DC coil system.

Photodetector

The system shown in FIG. 2 utilizes a differential photodiode circuit as a photodetector 216. As a result, the common mode signal due to the laser modulation can be efficiently rejected. Additionally, those skilled in the art will appreciate that other detectors, such as a balanced photoreceiver or a single-ended detector, could also be utilized in a chiral detection system in accordance with the principles of the present invention.

Figure 14:
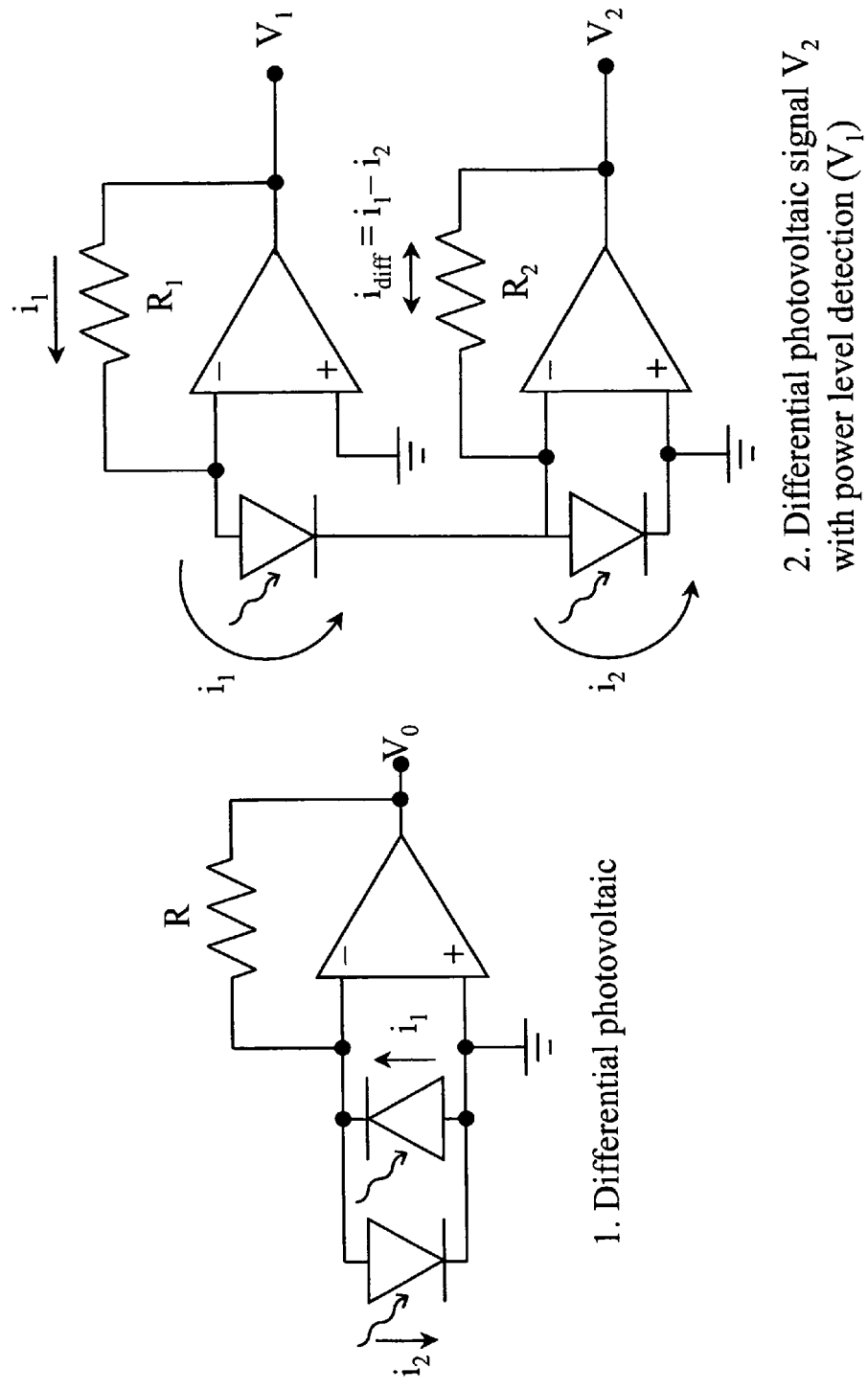
FIG. 14 is a series of diagrams on exemplary differential photovoltaic detectors that may be used in a chiroptical detection system in accordance with the principles of the present invention.

One embodiment of the present invention uses photodiodes in the photovoltaic mode as part of the photodetector 216. FIG. 14 shows further schematic details of exemplary differential photovoltaic detectors that may be used as photodetector 216. The use of such differential photovoltaic detectors has the advantage of providing a larger linear range due to their low series resistance and improved S/N (due to lower noise and minimal dark current from voltage bias). Where the signals of interest are in the audio frequency, the use of oversized diodes may allow a relaxation of beam alignment requirements. In other embodiments, smaller photodiodes with bias may be used to enhance the response to fast signals (e.g., >300 kHz). Also, by utilizing a larger capacitor in the feedback loop of the op-amp (clamps voltage to zero for a larger linear range), the input frequencies to the detection circuits are effectively low pass filtered. For example, in one embodiment, the 3-db point is approximately 15 kHz so that none of the signals of interest are impacted while any signals above 15 kHz (e.g., laser noise, harmonics, etc.) are greatly reduced.

Filtering

The output of the photodetector is further processed to determine the chiral purity of the sample within the sample flow cell. In the system of FIG. 1, processing of the detected signal is shown being done by a spectrum analyzer 110. In the system of FIG. 2, processing of the detected signal is shown being done by a lock-in-detector 210. Lock-in detector 210 extracts the signal amongst the various noise signals typically present by periodically modulating (e.g., using a square wave, sine wave, periodic pulse, etc.) some aspect of the chain, leading to a sinusoidal modulation to the signal. The lock-in detector then multiplies the signal by a nearly ideal sine wave of the same frequency (its "reference wave"), and then it integrates over a short time (but over many periods of the sine wave). If a particular signal occurs at the correct frequency, and if it is in phase with the lock-in sine wave, then it yields a large result. On the other hand, any signal (or noise) at the wrong frequency (or the wrong phase) integrates to zero because the product of this signal and the lock-in sine wave is as often positive as it is negative. Thus, only noise of the correct frequency (and phase) contributes and results in much less noise being detected relative to the signals of interest. As a result of using lock-in detection, much weaker signal levels can be detected because the lock-in amplifier acts like a bandpass filter with an exceptionally large Q (>100). Furthermore, the additional phase information is an additional source of information not present in typical filtering.

In an embodiment, the signal processing for such lock-in detection may include a filtering scheme that selectively filters and amplifies the signal being processed. As there may be several signals of interest with different relative strengths, selective filtering of the signal prior to digitization by an analog-to-digital converter (ADC) allows optimum levels of gain to be applied by individual amplifiers to each filtered signal. As stated previously, the amplification circuitry may provide low-pass filter circuitry (or have the effect of pre-filtering the signal) prior to providing the signal to the ADC. The ADC may also have circuitry for low pass filtering to reduce aliasing effects of the digitization. However, the relatively strong second harmonic of the optical modulator (2 w) would limit any gain for the other signals.

In one example embodiment, the signal from the photodetector may be first filtered in an ADC module. Basically, a filter may be used to further reduce the noise on the electrical signals prior to digital processing. While the type and specification of filter used in this embodiment may vary according to the system implementation, a preferred filter is a single active high pass analog filter used to remove undesired lower frequency signals and provide appreciable gain (with gain from an amplifier (not shown)) or at least minimal attenuation to frequencies above a preselected frequency.

The filter may also be implemented as separate filter chains providing different frequency characteristic signal outputs from each chain. FIGS. 9A-F illustrates various exemplary filtering schemes with filter chains in accordance with the principles of the present invention. FIGS. 9E-F are of particular use when using light modulation observed at 45°.

Figure 9A:
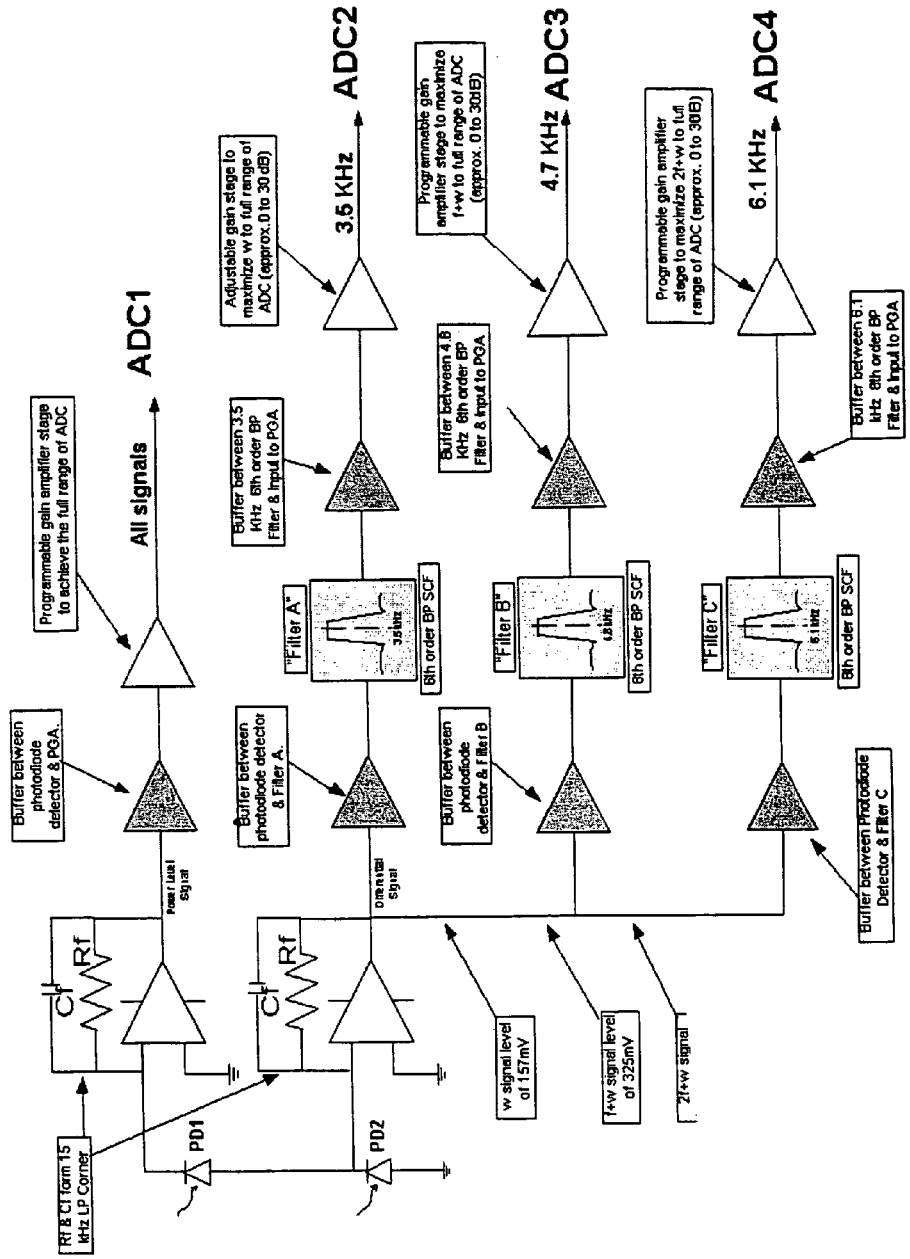

Looking now to the exemplary receiver block diagram and filtering scheme of FIG. 9A, a buffer resides between the photodetector and a programmable gain amplifier stage that provides a signal ADC1, which represents total power. In the lower chains, buffers are placed before and after each filter (i.e., filter A, filter B, and filter C). In this manner, the signal in each chain is respectively bandpass filtered for a desired signal. In the example illustrated in FIG. 9A, bandpass filter A is centered at 3.5 kHz and provides signal ADC2, which is correlated to α. Bandpass filter B is centered at 4.7 kHz and provides signal ADC3 at f+ω, which is correlated to a Verdet value. Bandpass filter C is centered at 6.1 kHz and provides signal ADC4 at 2 f+ω, which is also correlated to optical rotation.

The programmable gain amplifier mentioned above may also be used in each chain to provide the selective gain level. Typically, the gain levels are based on estimates of the maximum signals expected from the system response. In one embodiment, band pass filtering utilizes switched-capped capacitors as these have several advantages over the more common analog op-amp schemes (e.g., temperature stable, adjustable center freq, only external resistors for higher tolerance specs no external caps). In this manner, the filter (including individual filters and amplifiers in each chain) addresses noise issues before the input signals are digitized by analog-to-digital converters (ADC). Thus, the system is able to selectively amplify signals (i.e., ADC1-4) that vary as the chiral concentration and chiral ratios vary while also being able to attenuate the others.

Figure 9B:
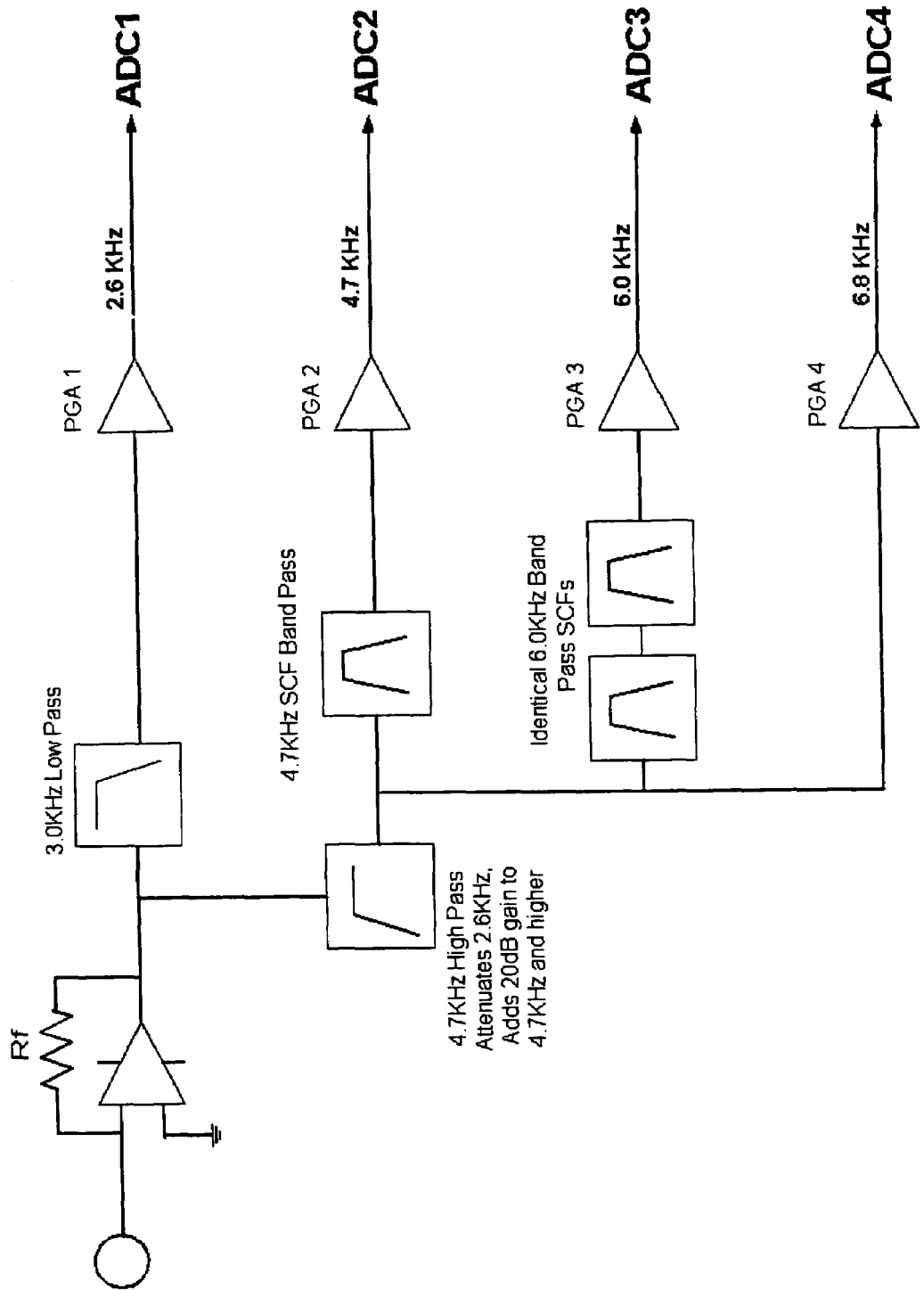
Figure 9D:
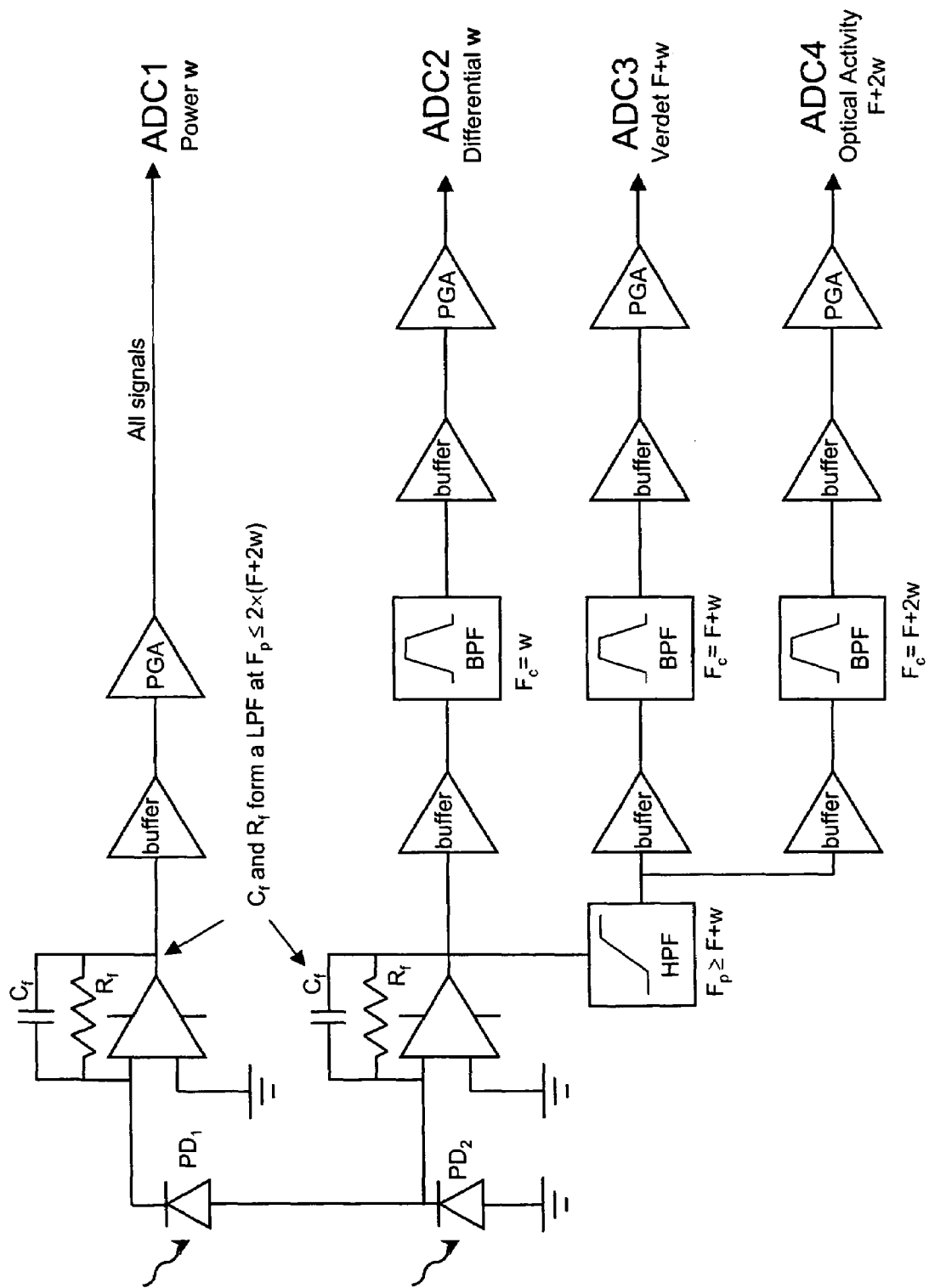
Figure 9E:
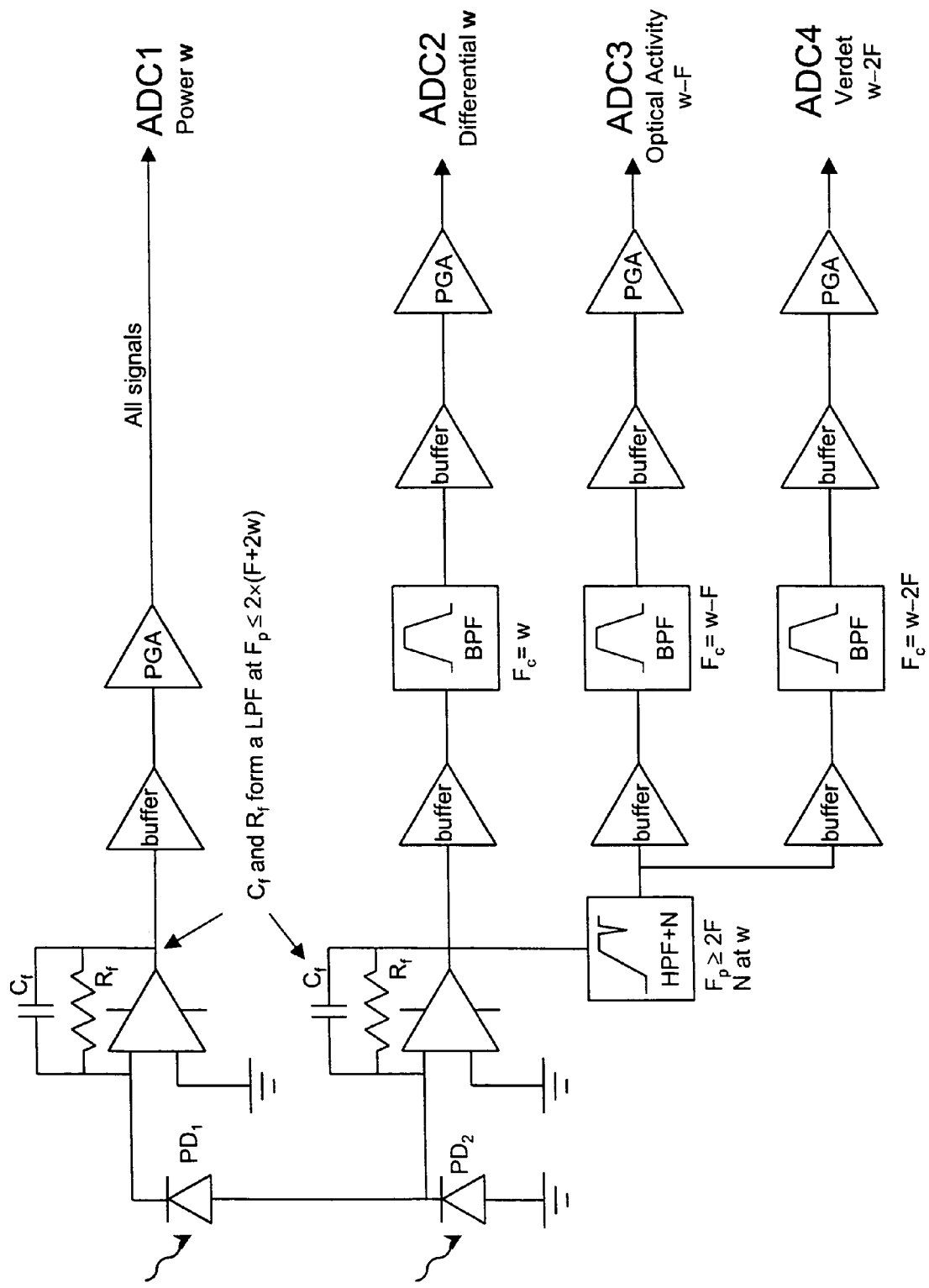
Figure 9F:
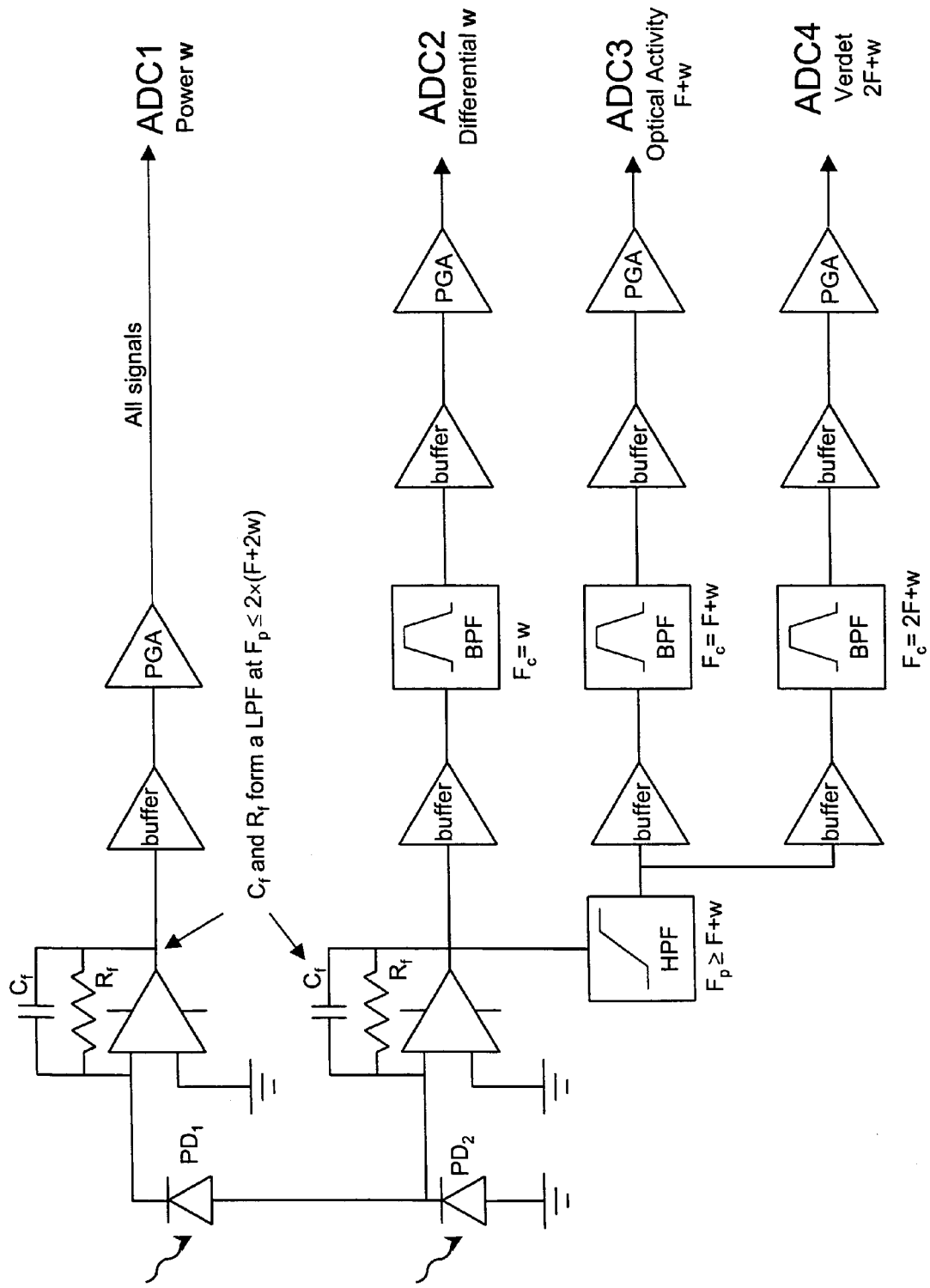
Figure 11A:
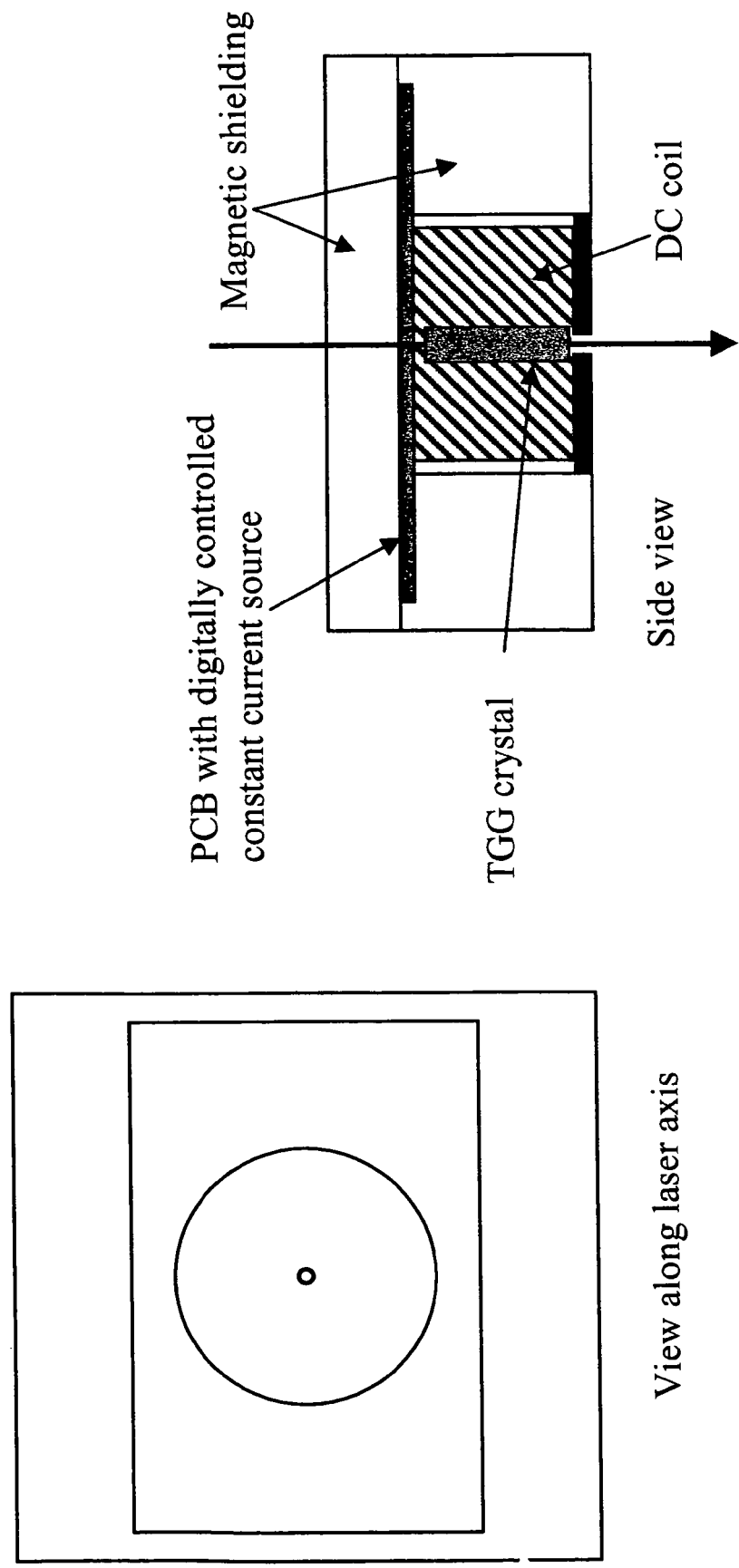
FIGS. 11A-H are various diagrams of embodiments of the DC null adjust module in accordance with an embodiment of the present invention.
Figure 11C:
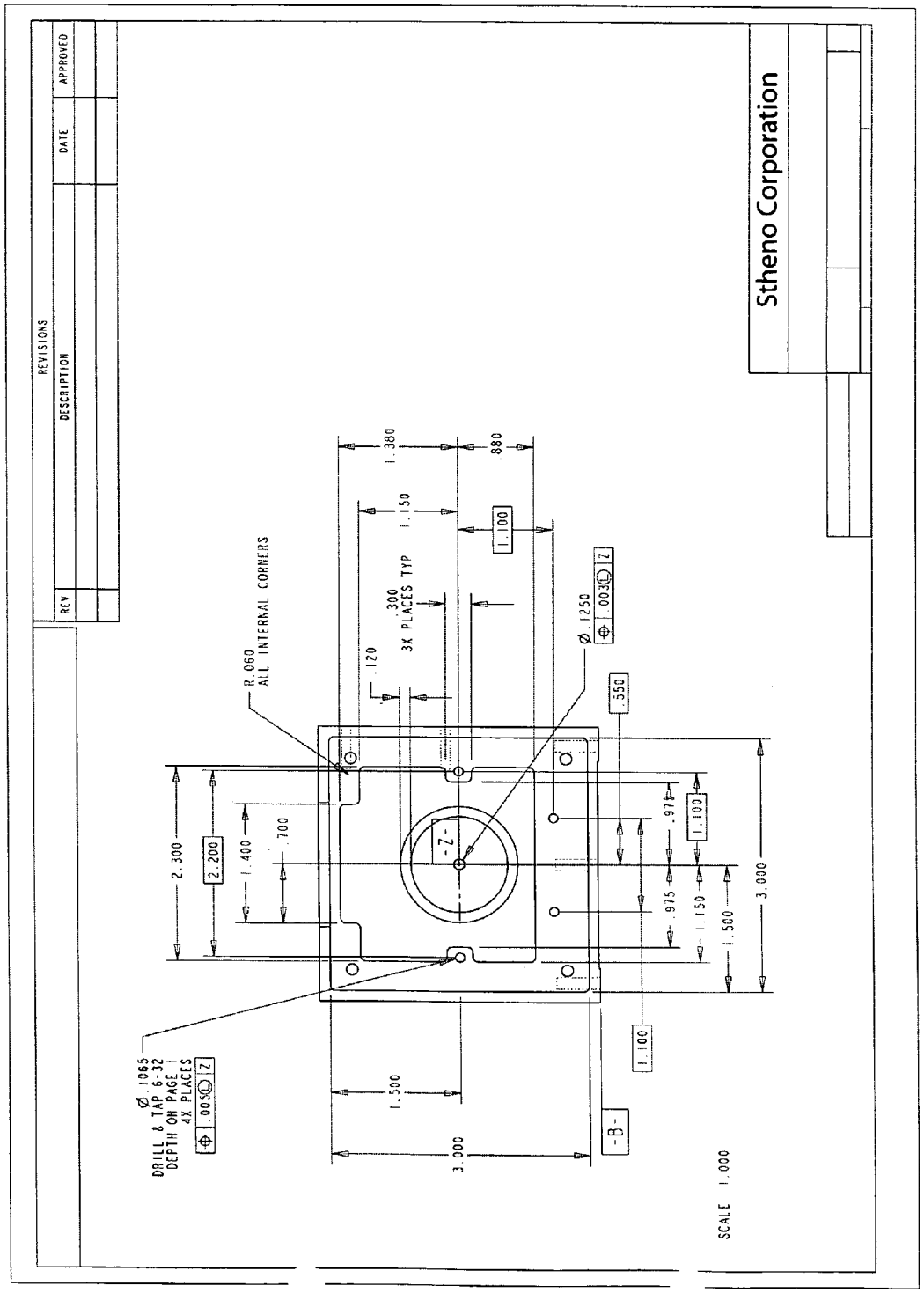
Figure 11B:
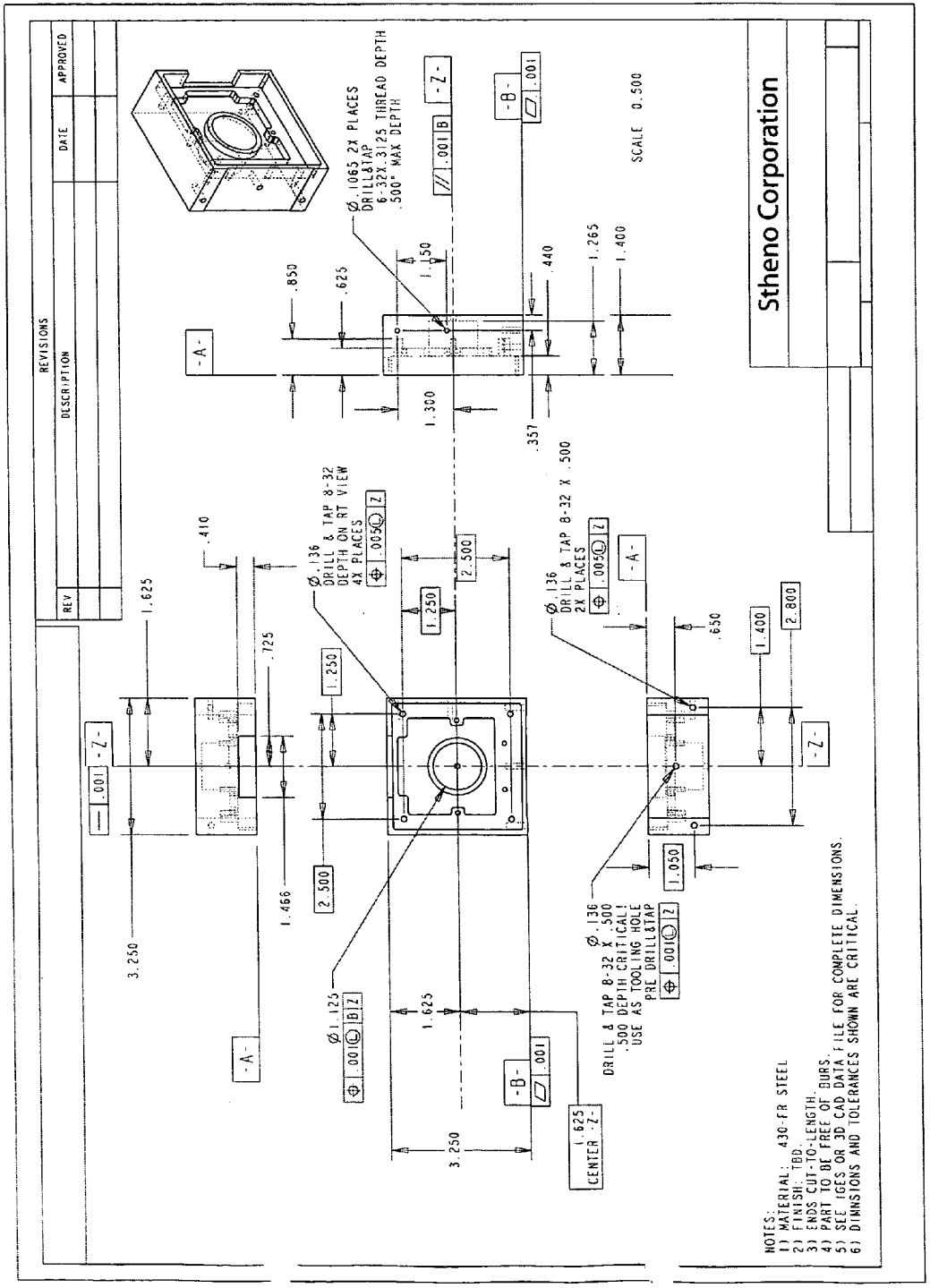
Figure 11D:
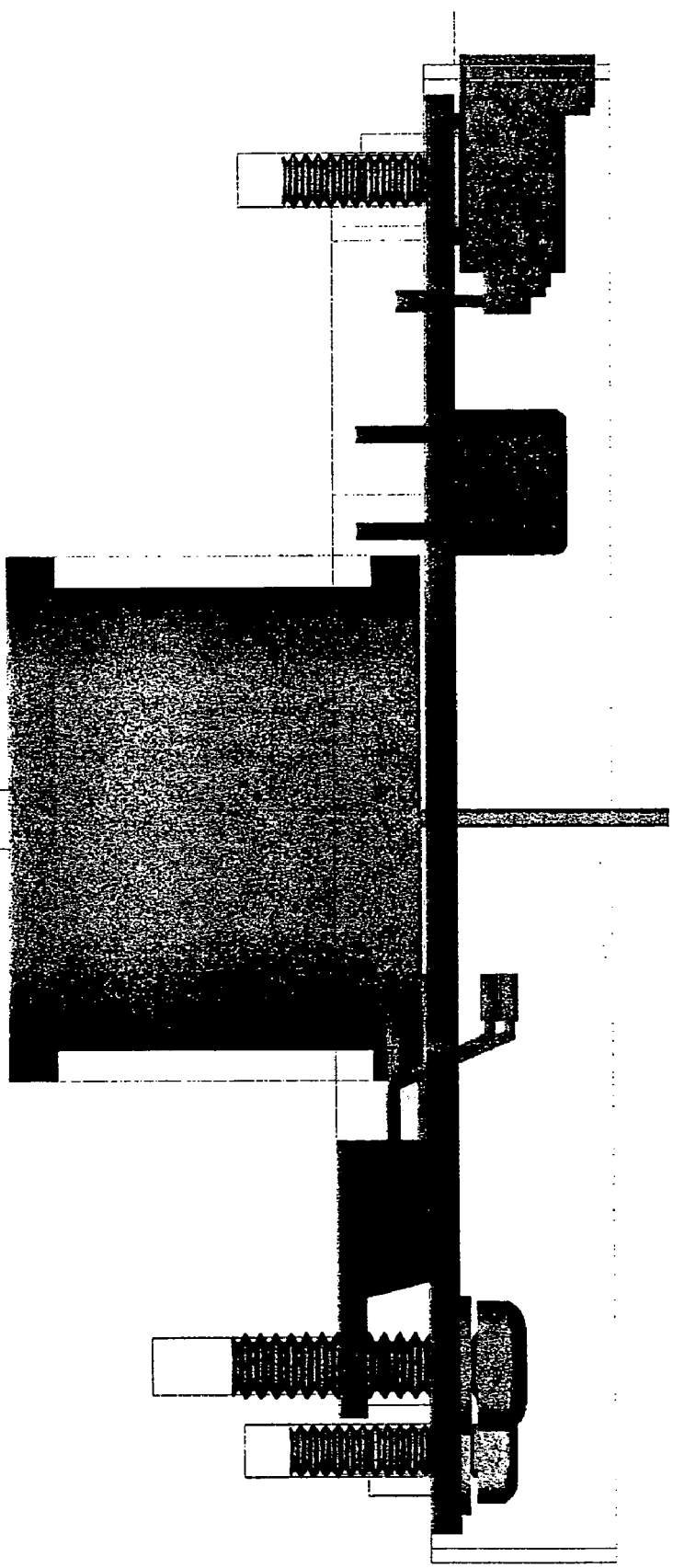
Figure 11E:
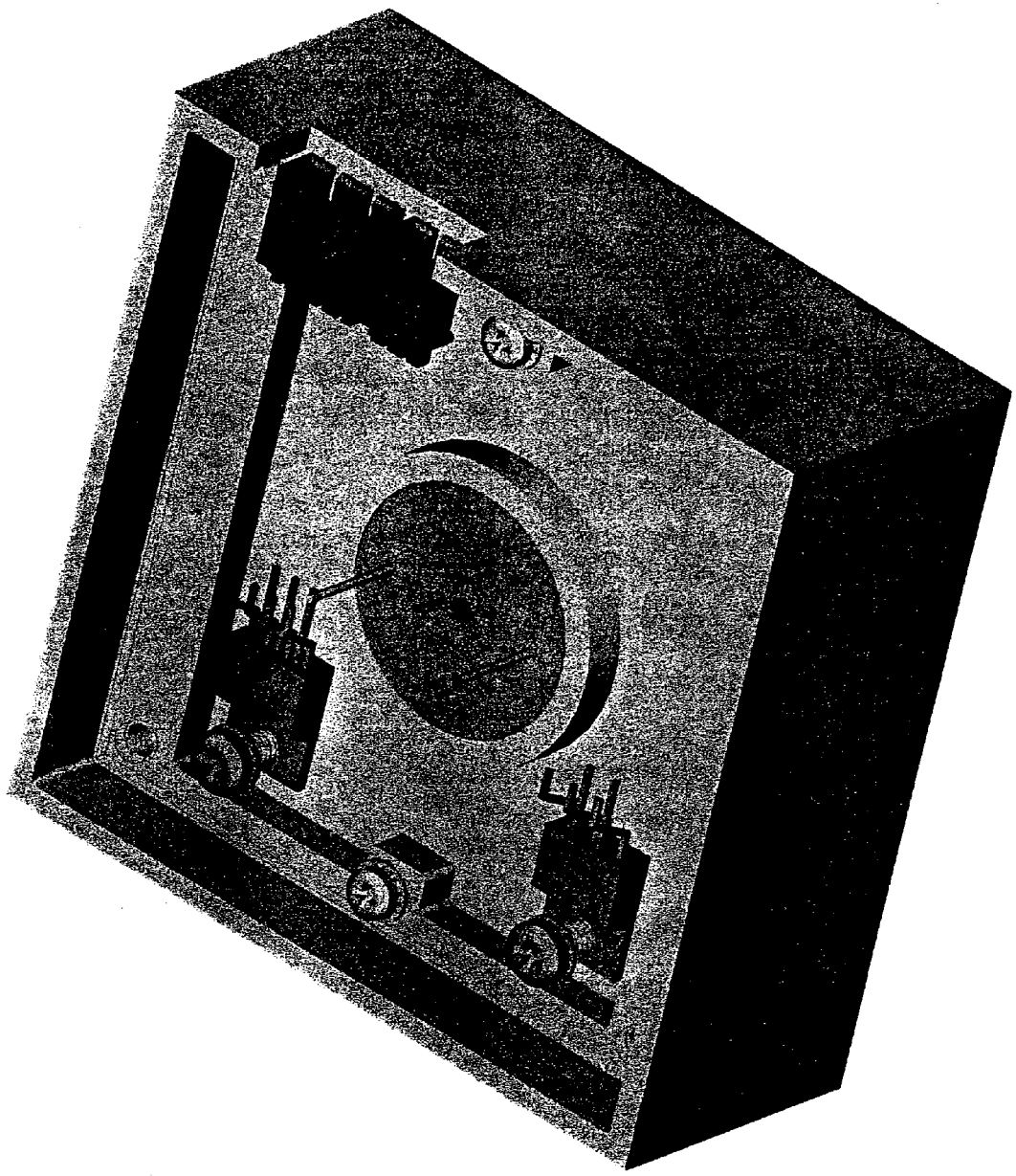
Figure 11F:
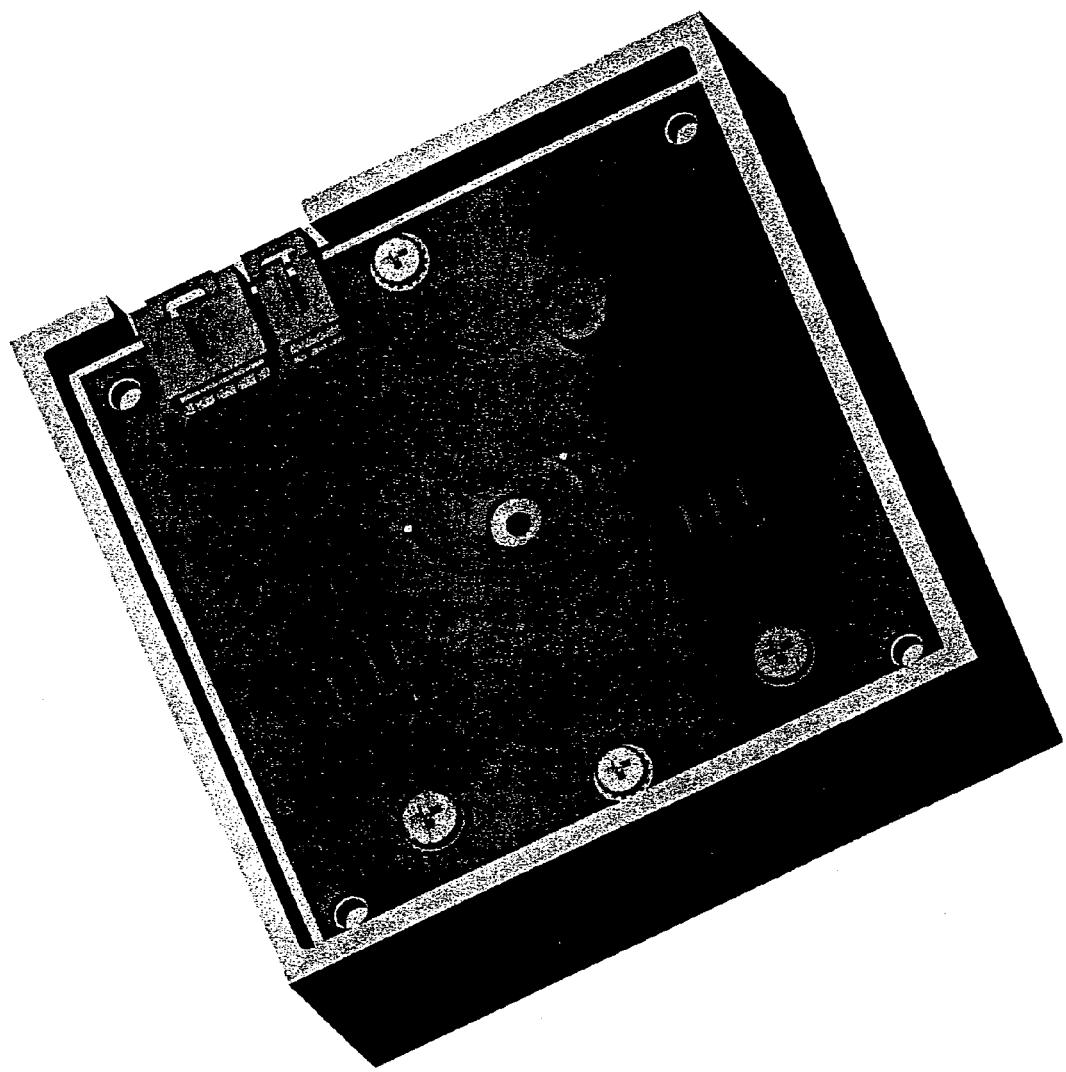
Figure 11G:
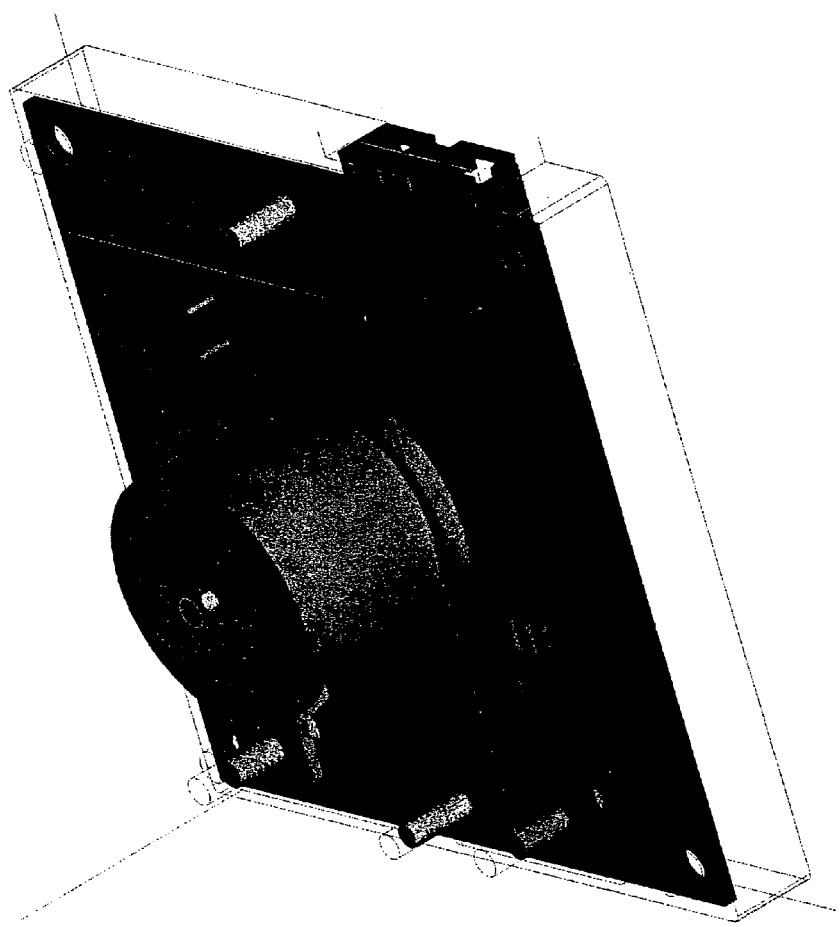
Figure 11H:
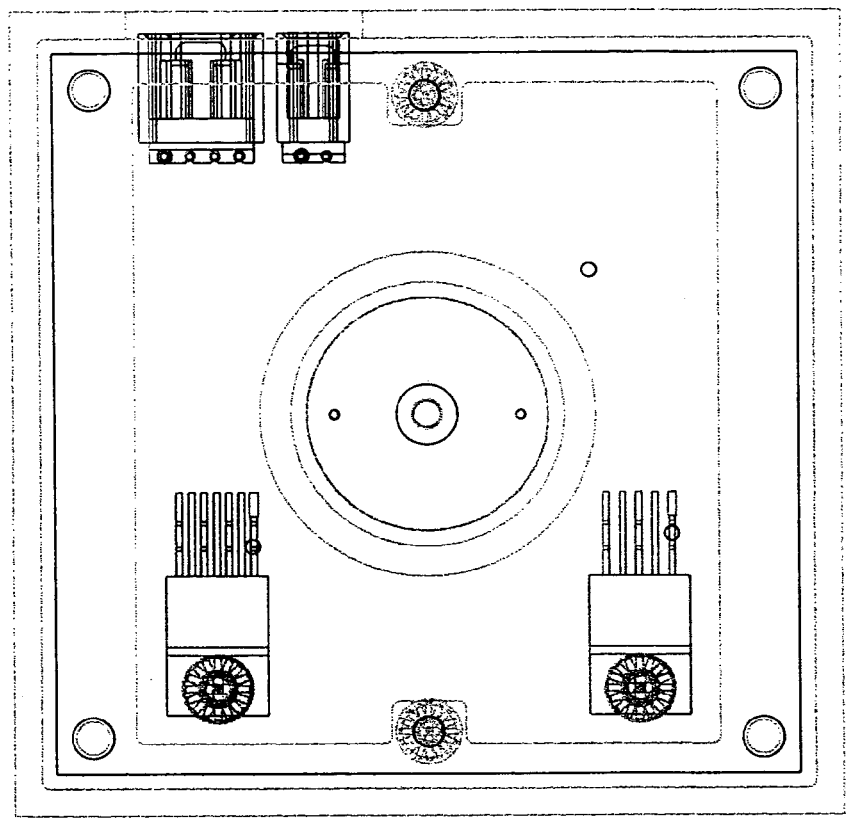

Referring now to FIG. 9B, another filtering scheme is illustrated. In this configuration, the output from the photodetector is passed through a 3.0 kHz low pass filter and a programmable amplifier to provide ADC1 at 2.6 kHz, a second harmonic of the light modulation and the value of which represents a total intensity value. In the lower chains, a high pass filter is used to feed separate filter chains, each of which are optimized to provide gain to a desired frequency for that chain, while minimizing the gain of the undesirable frequencies. In the illustrated example, this high pass filter allows a 4.7 kHz and 6.0 kHz parts of the signal to be separated from a 2.6 kHz part of the signal. Additional bandpass filtering allows the 4.7 kHz and 6.0 kHz signals to be extracted from each other and separately amplified to provide as ADC2 and ADC3, respectively. ADC2 represents f+ω and provides a measurement correlated to the Verdet value. ADC3 represents f+2ω and provides a measurement correlated to α. While the bandpass filter for the 6.0 kHz chain is illustrated as being implemented with two identical filters, it is contemplated that a single SCF bandpass may be desirable as well. A 6.8 kHz signal ADC4 (second harmonic of sample modulation) may also be utilized for a diagnostic tracking of the reference waves applied to the system.

FIGS. 9C-9F show additional alternative configurations for exemplary filtering schemes in accordance with the principles of the present invention. In these additional filtering schemes, other filtering schemes provide desired signals that may be used to indicate the chiral properties of the sample under test. Those skilled in the art will appreciate there are a variety of filtering schemes that may provide signals indicative of harmonics and intermodulation products of interest that are related to chiral properties of the sample. Additionally, while 1.3 kHz is for sample modulation (f) and 3.4 kHz would be for the laser or light modulation (ω), those skilled in the art will appreciate that the precise frequencies used in the illustrated examples are exemplary and not limiting with regard to the principles of the present invention.

As a result, exemplary detection systems can take advantage of reduced board complexity, utilization of higher tolerance parts (resistors, no caps), temperature stability, and tunable center frequencies controlled by an external reference clock. This allows the filtering scheme to be optimized to the actual tuned resonant frequencies in the system's modulators and changed whenever the system is retuned. Additional information on such retuning is described in U.S. Provisional Patent Application No. 60/584,233 and is hereby incorporated by reference. In addition, if different laser input powers change the gain requirements, the board can be adjusted in production by altering component values and not require a new board layout.

Digital Processing

Those skilled in the art will appreciate that digital filtering may be used instead of or in addition to such analog filtering to further enhance noise rejection and sensitivity of the apparatus. Digital filtering may be implemented using a digital signal processor (DSP) (see FIG. 10). Those skilled in the art will understand how processing of the digitized signal may be accomplished with a digital signal processing (DSP) module, which may use a specialized processor, memory and interfacing logic to handle the filtering, processing and/or feedback functions in an exemplary chiral detection system.

In addition to digital filtering, a DSP may be used for improved signal processing and chiral detection. In one embodiment, the location of the DSP on the module (or board) with the filtering allows near real-time analysis of the input signals utilizing a double lock-in analysis (as described in U.S. Provisional Patent Application Ser. No. 60/568,104) and active single frequency cancellation (U.S. Provisional Patent Application Ser. No. 60/584,232). The processed signal is normally output to the GUI display on the chiral detection system (see FIG. 15) along with an analog output on the back of the instrument. Other embodiments may also output a digital signal so as to maintain superior S/N.

In more detail, the analog output is a way for the chiroptical detection system to communicate the calculated information on the Optical or ee % measurement (user can chose one channel A output) described previously and the Verdet measurement (the user can chose one channel B output of an external ADC box compatible with the users software). The only difference on the Verdet measurement is whether the user wants the additional phase information or prefers doubling the dynamic range (0 to 1 V input typical) into his ADC by only taking the absolute value (if used solely for concentration). This analog output has the advantage of supporting legacy equipment lacking digital communication and avoids the necessity of the FDA 21 CFR Part 11 validation required for direct digital communication. As mentioned above, other embodiments will directly output a digital signal complying with 21 CFR Part 11 in addition to analog output for legacy systems. This direct digital output has the advantage of avoiding S/N degradation inherent in outputting an analog signal.

In one embodiment, the data conversion path from the chiroptical detection system is analog (photodiode/pre-ADC filtering) to digital (ADC/DSP) to analog (DSP/DAC+filtered and buffered output) back to digital in the users' ADC+computer data acquisition. In other embodiments, the system may desirably be implemented such that the data conversion path stays digital after DSP processing for optimal S/N characteristics and more dynamic range flexibility during an experimental run.

Figure 15:
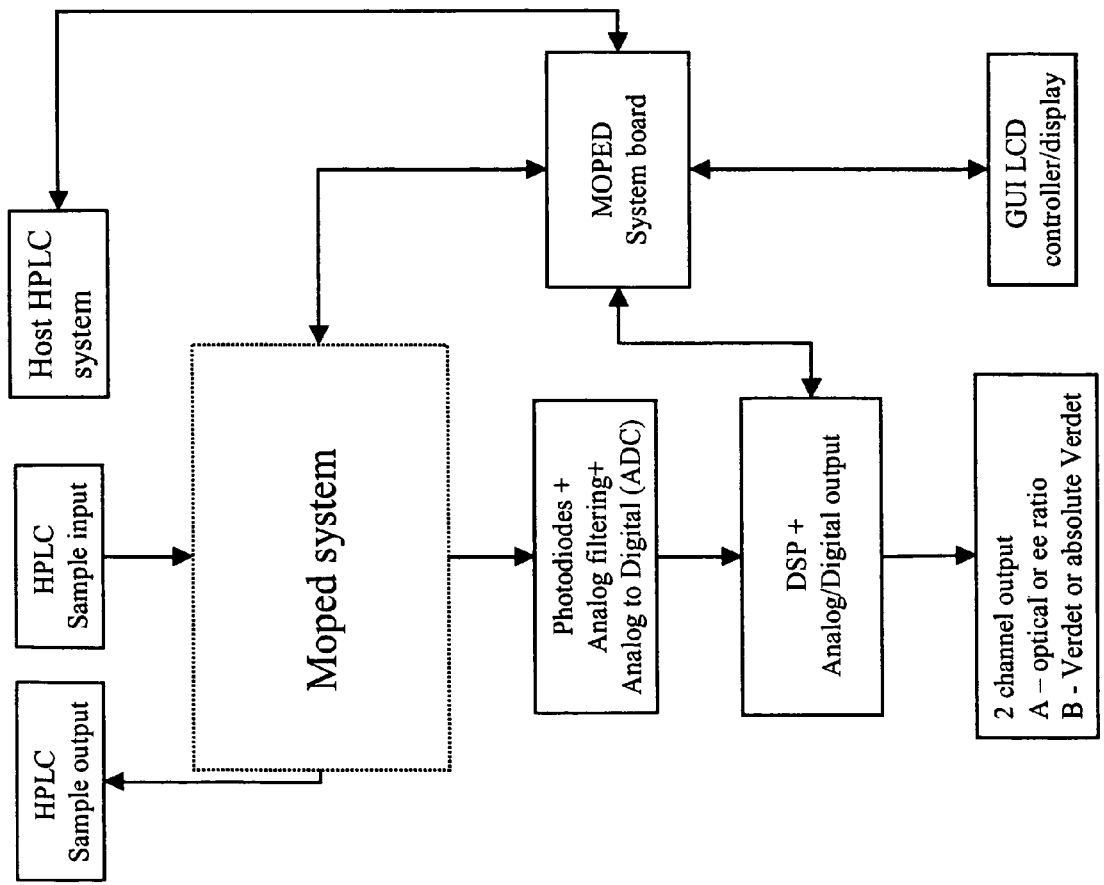
FIG. 15 is an exemplary operating environment for a chiroptical detection system including a graphical user interface and input/outputs that may connect with user systems in accordance with principles of the present invention.

In another embodiment, the instrument may output two signals as shown in FIG. 15 and have two options for each.

Referring now to FIG. 15, the DSP communicates with the system board to output information to the GUI but the data collection may be done by the user's ADC converter box (not shown, but typically implemented with a 24-bit, 0 to 1 volt input, up to 100 Hz sampling rate ADC). These signal outputs, channel A (optionally showing optical activity or ee %) and B (optionally showing Verdet or absolute value of Verdet), are also provided as two separate channel outputs (A and B) by the DSP controlling a DAC (digital to analog converter) that is low pass filtered (i.e. 1 kHz LPF) to remove high frequency DAC noise. This LPF output may then be sent through a buffering stage to provide an output impedance of 50 ohms. This prevents loading of the DAC and prevents overdriving the user's ADC by limiting output voltage to predefined range (0 to 1 V).

In one embodiment, the optical signal for channel A will be the $(\phi+2\omega/2\ \omega)\times(\pm\phi+2\ \omega\ phase)$ and this will track the optical activity of the sample normalized for variations in light intensity. A second option for this channel is $(\phi+2\ \omega/f+\omega)\times(\pm\phi+2\ \omega\ phase)$, which gives an optical activity signal normalized for the chiral component concentration and, hence, is directly correlated to ee %. Changes in light intensity should not affect this ratio, but the signal can be normalized by $2\ \omega$, if necessary.

The second channel (channel B) utilizes $(\phi+\omega/2\ \omega)$ and this signal is directly correlated to sample concentration based on the Verdet signature (no absorption needed). A second option for this concentration measurement is $(\phi+\omega/2\ \omega)\times(\pm\phi+\omega\ phase)$, which allows additional discrimination between species based on their respective Verdet relative to that of the carrier fluid (i.e., the relevant measurement for a particular species is the difference between the Verdet associated with the carrier fluid when carrying the sample and the Verdet of the carrier fluid without the sample). The trade off between the two choices is that the simple $(\phi+\omega/2\ \omega)$ assumes concentrations are always positive and can use the full linear range of the output whereas the $(\phi+\omega/2\ \omega)\times(\pm\phi+\omega\ phase)$ gives more information but any particular peak can only span 0 to +0.5 (negative) or +0.5 to +1.0 (positive), thus, causing dynamic range compression. The optical activity and ee % signal will have this property during half of the periodic range at the output (0 to +0.5 (negative) or +0.5 to +1.0 (positive)) since both natural optical rotation and ee % can be positive or negative.

Ferrite Inner Shield

In an additional embodiment of the invention, a second inner shield is added between the coil and the metal housing mounted to the optical rail. This inner shield is can be made from material with higher volume resistivities, such as ceramic ferrites, and high permeabilities but lacking the mechanical properties necessary for mounting to the optical rail. Since the outer shell provides a robust mounting surface and the inner shell can be machined or formed to match the inner surface and coil dimensions, this limitation of the magnetically more desirable ceramic materials is overcome. One advantage of using such a second inner shield is a lower eddy current loss from the double shield and higher internal magnetic fields achieved with the same input power. Additionally, the double shield provides better magnetic isolation that a single shield composed of either material (magnetic SS or ceramic ferrite) and advantageously allows one to utilize nonmagnetic metals for the outer shield if desired (slightly lower eddy current losses but slightly higher magnetic leakage).

Thermal Equilibration of the Input Sample

A potential source of baseline noise in the system was attributed to thermal variations in the inflowing sample stream. As refractive index of the fluid is dependent on temperature, these variations can show up as spurious pseudorotations in the optical signals. While the sample flow cell can be designed to reduce the impact of refractive index changes in the sample fluid, achieving thermal equilibration of the inflowing sample prior to introduction to the optical path was shown to drastically reduce this baseline noise/drift. In an additional embodiment of the invention, an exemplary method of thermally equilibrating the input sample was to wrap the input tubing around the central spindle in an air gap provided by increasing the magnetic coil ID. This additional path length allows the flowing fluid to reach thermal equilibrium with the sample modulator system prior to interacting with the probing beam along the central axis of the sample cell. In another embodiment, preheating the sample prior to introduction was also investigated and found to improve noise due to thermal variations in the external sample fluid temperature. However, the implementation of the passive equilibration has the advantage of being simpler and more robust. Additionally, a passive countercurrent heat exchanger was added to the inlet and outlet fluid paths by thermally contacting the inlet and outlet tubing (see exemplary tubing in FIG. 6A). In one embodiment, this thermal contacting was accomplished by twisting the inlet and outlet tubing around each other in a braided fashion, covering the tubes with thermal grease, wrapping this construct with braided copper wire, and covering this with thermoshrink tubing. An assembly of approximately 3 inches in length was found to be adequate for passive thermal preheating by this countercurrent heat exchange. Alternative embodiments may be implemented with other thermal insulators and heat exchange structure configuration (side-by-side, etc.). In some embodiments, thermally contacting PEEK or stainless steel tubing that are contacted with thermally conductive materials, (e.g., thermal paste) and surrounded with insulation to isolate the passive heat exchanger from variations in external temperatures may be utilized.

Backpressure Regulator Downstream for Pulsation Improvement

Another potential source of baseline noise in the system was attributed to pressure pulsation due the HPLC pumps (not shown) upstream of the detector. Those skilled in the art will be familiar with conventional HPLC systems, including such pumps. This pulsation noise is thought to come from refractive index changes of the fluid due to disrupted thermal equilibration or pressure effects flexing the optical windows inducing birefringence. In one embodiment, in order to reduce the impact of these effects, a back pressure regulator (BPR) may be added to the sample flow path downstream of the sample cell. This low swept volume maintained between 100 and 500 psi on the sample cell with a recommended flow rate range of 100 μl/minute to 1 ml/minute and a max flow rate of 4 ml/minute. In addition, thicker optical windows (3 to 6 mm) may be utilized to increase the stiffness of the glass and reduce any pressure induced flexing of the window.

Refractive Index Minimization in the Sample Flow Cell

Refractive index (RI) effects can cause spurious noise signals in the optical rotation measurements due to a phenomenon known as pseudorotation. U.S. Pat. No. 5,168,326 describes one method for the reduction in RI effects by restricting the inlet channel relative to the flow channel. However, the method described therein does not describe muting the RI effects as contemplated in the present invention.

In one embodiment of the present invention, radial mixing of the input stream is promoted to disrupt the formation of lensing effects from RI gradients in the flow cell. To achieve this, a central path may be established to set up a double vortex mixing pattern along the bore of the flow cell. This radial mixing approximates the benefits of turbulent mixing plug flow in disrupting lens effects from RI gradients resulting in laminar flow even though the fluid regime is well within the laminar flow range. In another embodiment, the sample flow cell has been shortened (9 cm to 5 cm) and the diameter increased (0.75 mm to 1.25 mm) to further reduce the impact of RI lensing during analysis. In another embodiment that encourages mixing, the inner glass capillary is treated with an acid (e.g., HF acid) to etch the smooth surface and change the fluid flow regime disrupting laminar flow. However, this modification may increase the depolarization effects of scattered light and, thus, is particularly useful for large diameter sample flow cells where the light beam does not substantially interact with the flow cell wall. Alternatively, increasing the scattering of light that hits the cell walls can decrease depolarization noise as this light is so highly scattered it never reaches the detector.

Additional Sample Flow Cell Modifications

In an additional embodiment of the invention, the shape of the central flow cell can be optimized to reduce RI effects and reflected polarization noise. A truncated cone has been shown to reduce RI effects in prior systems utilizing analytical flow cells for absorbance and fluorescence measurements. Three exemplary truncated cones or flow cells used in prior systems to reduce RI effects are shown in U.S. Pat. Nos. 4,276,475, 4,011,451, and 6,307,204. This geometry of the flow cell reduces the lensing effect by increasing the cross-sectional area as the fluid flows from the inlet to the outlet. This increasing cross-section tends to flatten the lens caused by RI effects and, thus, reduces the impact pseudorotation noise on optical rotation measurements. In addition, if the probing light propagates parallel to the fluid flow in the direction of increase cross-section, the tapered walls reduce potential interactions with the light that can be scattered to the detector. Prior to this work, the advantages of tapered flow cell construction have not be utilized in polarization measurements due to the requirement for relatively long path length interactions to achieve detectable optical signals. In one example, a truncated flow cell taper of 1 to 3 degrees increases volume drastically over the typical polarimetric flow cell lengths of 5 to 10 cm. Given that small sample cell volumes (5 to 100 ul) are required for analytical work, tapered flow cells have not been utilized for polarimetric measurements. In contrast, a chiroptical detection system according to principles of the present invention can compensate for a shorter path length by increasing the applied field. The Verdet signal scales linearly with field and length and the optical signal scales linearly with length but with the square of the field. In one embodiment, it is contemplated that a truncated cone shaped flow cell may be manufactured from stainless steel and with a reduced length of the cell by using an air gapped magnetic design for the cell. Thus, for optical activity measurements, the benefits of a truncated flow cell geometry can be advantageously used and the results more than compensate for the reduced optical length.

Figure 17:
FIG. 17 is an exemplary assembled flow cell in accordance with an embodiment of the present invention.
Figure 18:
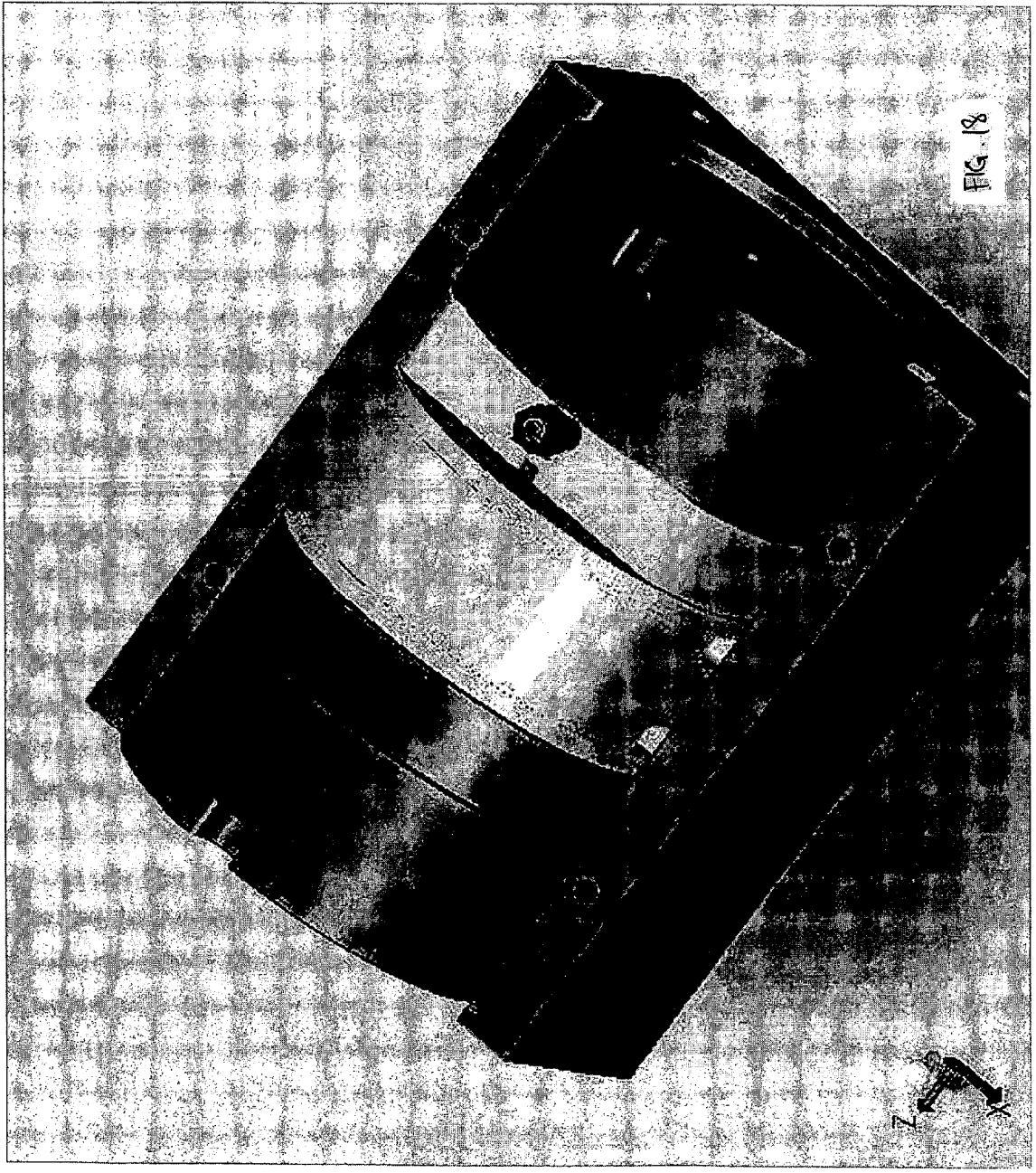
FIG. 18 is an exemplary assembled flow cell in shells in accordance with an embodiment of the present invention.

Two exemplary flow cells used in accordance with an embodiment of the present invention that are not truncated cone shaped are shown in FIGS. 17 and 18. FIG. 18 show the flow cell as it appears within a shell.

Magnetic Coil Modifications

In an additional embodiment of the invention, the flow cell path length is reduced by shortening the central spindle and increasing the magnetic field. The increased magnetic field is accomplished by gauge magnetic wire (#26, #28, #30, or #32) wound onto a plastic bobbin to provide structural support. The finer gauge wire is not amenable to orthocyclic winding for self supporting air core coils. Thus, computer layered winding onto a bobbin support is an alternative. The benefits of reducing the wire size allow a lower current to achieve the same field since amp-turns establish the strength of the magnetic and the additional turns compensate for the reduced current. Additionally, the dissipated heat at the coil is greatly improved for the same field since the power losses scale as the square of the current and linearly with resistance. The additional impact of proximity effect losses is also reduced as the current is lowered. Skin effects can also come start to contribute losses but for the low audio frequencies used in such multi-layer windings, the proximity effects are the larger contributor for coils losses. Therefore, it has been found that lowering the gauge and increasing the windings is advantageous with the only limitation being that the driving voltage required increases and breakdown voltage of the windings can be exceeded in the resonant circuit beyond a critical applied voltage.

Driving Frequency Modifications

The two reference waveforms applied to the system would ideally be perfect sine waves as all of the waveform energy is contained in the fundamental frequency. However, as all amplifiers have some harmonic distortion and laser diodes do not behave linearly to zero output, the driving frequencies will have non idealities associated with the real waveforms modulating the system. Therefore, filtering the waveforms after generation or driving the system with non-sinusodial waveforms has advantages in reducing noise in regions of interest for signal analysis. Because noise and higher order harmonic frequency components may be filtered during signal analysis, an embodiment of the present invention may opt to use square waves to modulate the system for ease in digitally manipulating the laser.

One instance of the benefits of filtering post waveform generation occurs on the waveform driving the magnetic field. The DAC generating the waveform has limited bit resolution (e.g., 10, 12 or 24-bit) and the amount of harmonic distortion added is inversely proportional to the bit resolution. Those skilled in the art will appreciate that one may reduce distortion by increasing the bit resolution or, more conveniently, low pass filtering the DAC output to remove harmonic distortion. In one embodiment, the resonant system modulating the sample cell also acts as a low pass filter attenuating any harmonic distortion added by the power amplifier. The harmonic distortion added by power audio amplifiers is usually very low and optimal around 1 kHz since this is the test tone frequency where comparisons are made between different audio amplifiers. In embodiments of the chiroptical detection system of the present invention, modulations of distortion free sine waves below 500 Hz tend to be more difficult to produce electronically so choosing a modulation frequency >500 Hz is desirable from a harmonic distortion perspective.

The modulation waveform on the laser can be sinusoidal, square wave, or arbitrary. Driving with a sinusoid produces harmonic distortion as the laser behaves nonlinearly at low driving currents (e.g., become LED-like). Alternatively, driving with a square wave should produce only the fundamental plus odd harmonics. However, in practice the diode laser was observed to contain some second harmonic content under both driving waveforms and this was found to limit amplification of the 2 f+w optical signal due to the relatively large 2 w signal only partially attenuated by the 2 f+w bandpass filter.

In addition, production of an ideal or substantially perfect square wave from clock division or wavetable synthesis to produce an even frequency wave was found to be problematic (e.g., frequency jitter or waveform discontinuities within table). Therefore different waveforms and laser modulation types (analog vs TTL) were tested and a band limited square wave or a sinusoid with a DC offset generated by wavetable synthesis were found to provide a desirably low noise floor and minimal second harmonic content. The band limited square wave advantageously allowed accurate wavetable synthesis while producing less 2 w signal than other tested waveforms. The output from the DAC was low pass filtered to attenuate harmonic content above 11 w (i.e., 11th harmonic of w). This retained the square wave nature of the wave while removing high frequency noise added by the DAC synthesis. The modulation type of the driving circuitry on the laser (analog vs. TTL) was not found to significantly impact performance of the bandlimited squarewave. The sinusoid waveform's DC offset was adjusted to reduce distortions caused by nonlinearities of the laser diode at low driving currents. In one embodiment, these optimized DC offset sinusoids were able to deliver about 70% of the laser power (continuous wave) to the fundamental driving waveform. In addition, the SCF bandpass filter for the 2 f+w optical signal was narrowed from a Q=20 to Q=25 (Quality factor $Q=f_c/BW$ where $f_c$ is center frequency and BW is the bandwidth defined by the upper and lower cutoff frequency) in this embodiment to further attenuate the remaining 2 w second harmonic component.

Reduced Laser Excess Noise

In an embodiment of the system using a balanced photodetector, the balanced detection of the photodiodes greatly reduces common mode noise due to laser intensity fluctuations (laser excess noise). However, as the photodiodes may not be perfectly matched, further means of reducing the laser excess noise are desirable. In one embodiment, a method of increasing the signals of interest relative to this laser excess noise has is to attenuate the carrier polarization component while preserving the modulated polarization component (e.g., Y main component, X minor component orthogonal to Y). This can be accomplished by placing an additional polarizer (not shown) in front of the Wollaston beamsplitter (e.g., Wollaston polarizer 208). Ideally, this component will be orthogonal to the input polarizer for maximum attenuation of the major polarization component and minimum attenuation of the minor component carrying the signal of interest. This is particularly advantageous for reducing excess light noise since the noise is decreased linearly with the attenuation while the signal of interest is only reduced as the square root of the attenuation. Thus, the signal-to-noise (S/N) ratio improves as the square root of the attenuation of the input polarization. The filtering scheme utilized in this dual polarizer setup is shown in FIG. 9F for the +sidebands and FIG. 9E for the −sidebands.

Carrier Frequency Normalization

While observing at the inter-modulated sidebands greatly reduces the background noise, slow variations in laser intensity and optical losses in the system may still undesirably influence the recovered signal. In one embodiment of the present invention, the carrier modulation of the laser light can be utilized to normalize these noise contributions from the detector output. Thus, the ratio of the signal magnitudes at the sidebands containing the optical and Verdet signatures to the recovered magnitude at the laser modulation frequency is immune to laser power variations and optical losses in the system (e.g., f+w/w and 2 f+w/w for optical and Verdet when observed at null). The carrier frequency does not carry any phase information of relevance to the optical or Verdet signal of interest and so only the recovered magnitude is utilized for normalization. This normalization technique has been separately demonstrated in current sensor optical measurements utilizing the Faraday effect in optical fibers (Ferrari, J. A., et al (1999) Applied Optics 38 (13) pp 2606-2611). In another embodiment, the log ratio of the sidebands and the carrier frequency (i.e., log (f+w/w)) is utilized to linearize the normalized output.

Virtual Ground in Balanced Transimpedance Amplifier

While prototyping the balanced photodiode front end in an exemplary system, it was discovered that the virtual ground originally introduced for a power measurement, see FIG. 9E-F and FIG. 14, circuit 2 later supplanted by utilization of the differential carrier frequency magnitude, provided superior results to the simplified anti-parallel construct. While a simpler anti-parallel circuit was expected to have less noise due to the removal of voltage noise contributions from the virtual ground of the power monitoring op-amp, the simple anti-parallel construct showed distortion products absent in the virtually grounded circuit. These distortions are thought to arise from slight mismatches in the photodiodes series resistances. Simulations indicated that the virtual ground made the circuit less sensitive to small differences in photodiode series resistance (e.g., responsivity matched to less that 1% difference). Hence, a slightly more complex anti-parallel photodiode front-end with one photodiode utilizing a virtual ground from a low voltage noise op-amp provided a more robust and cleaner output than the simple anti-parallel photodiode architecture. In another embodiment, the slight mismatch in photodiode series resistances can be matched via a loaded pot at the summing junction of the photodiode currents.

In one embodiment, o-ring seals between the PEEK flow cell and windows were able to provide superior sealing without adding problematic stress induced birefringence in the thicker windows (6 mm). As o-ring seals are easily available in a variety of chemically resistant materials, this mode of sealing flow cell between the window and PEEK cell utilizing Kalrez or Teflon encapsulated viton o-rings was preferred over flat gasket seals and pure Teflon single-use o-rings. In an exemplary system, a standard 012 ASTM groove was utilized and machined directly into the PEEK surrounding the inlet and outlet fluid channels. The o-ring seal was then used in the groove.

In another embodiment, it was found that adding a pin hole prior to the Wollaston analyzing prism was advantageous for cleaning up the beam. In this manner, light that interacted with the flow cell walls or was otherwise corrupted in the beam path was prevented from reaching the photodetectors. In further efforts to reject reflected light, all surfaces in the light path were darkened. For example, such surfaces may be made matte black. This may be accomplished by applying a black marker pen, using black PEEK, using black viton, using black anodization of the aluminum, and/or using a black oxide treatment of the system's steel. In addition, the interior of the system's housing may be insulated to buffer outside changes in ambient temperature. The interior insulation may also be darkened, e.g., made matte black, to absorb any stray reflections.

The embodiments and examples described herein are meant to be illustrative and exemplary. Other embodiments of the invention will be apparent to those skilled in the art from consideration of the specification and practice of the invention disclosed herein. Accordingly, a true scope and spirit of the invention being indicated by the following claims.

What is claimed is:

1. An apparatus for detecting a chiral property of a sample, comprising:
    a captive guide structure having an elevated top platform and a dove tail construct disposed on ends of the elevated top platform, wherein the captive guide structure is made from a heat conductive material and the elevated top platform has a substantial width in comparison to a height of the elevated top platform;

a base portion supportive of the captive guide structure, wherein the base portion is made of a heat conductive material, has a width that is at least twice the width of the elevated top platform, and has a substantial thickness relative to the captive guide structure; and a plurality of elements operative to detect the chiral property of the sample, the elements being securely mounted on the captive guide structure, at least a portion of the elements being in direct thermal contact with the substantial width of the elevated top platform;

whereby the substantial width of the elevated top platform on the captive guide structure and the width and thickness of the base portion facilitate an enhanced dissipation of heat from the portion of the elements.

2. The apparatus of claim 1, wherein the plurality of elements comprise:

a) a light source for generating an input light beam;
b) a polarizer for converting the input light beam into a beam of linearly polarized light;
c) a sample compartment through which a modulated beam can pass to produce a signal beam;
d) a sample flow cell having an input chamber optimized for mixing the sample;
e) a sample modulator for magnetically modulating the sample within the sample flow cell;
f) an analyzer for splitting the signal beam into a first polarized signal beam and a second polarized signal beam;
g) a first light detector for measuring the light intensity of the first polarized signal beam and converting the light intensity into a first electrical signal;
h) a second light detector for measuring the light intensity of the second polarized signal beam and converting the light intensity into a second electrical signal; and
i) a processing circuit that determines the chiral property of the sample based upon values of the first electrical signal and the second electrical signal.

3. The apparatus of claim 1, wherein the captive guide structure and the base portion are collectively formed as a mounting rail for the elements.

4. The apparatus of claim 3, wherein the mounting rail includes a first portion for a first group of the elements and a second portion for a second group of the elements.

5. The apparatus of claim 4, wherein the first portion and the second portion are separately mounted onto a casing for the system.

6. The apparatus of claim 5, wherein the first group of the elements is operatively coupled to the second group of the elements.

7. The apparatus of claim 4, wherein the elevated top platform from at least one of the first portion and the second portion provides a heatsink for the respective ones of the elements in the at least one of the first portion and the second portion.

8. The apparatus of claim 1, wherein the width of the base portion is at least three times the width of the elevated top platform.

* * * * *

UNITED STATES PATENT AND TRADEMARK OFFICE
CERTIFICATE OF CORRECTION

| | | |
|---|---|---|
| PATENT NO. | : 7,468,788 B2 | Page 1 of 1 |
| APPLICATION NO. | : 11/471994 | |
| DATED | : December 23, 2008 | |
| INVENTOR(S) | : Gibbs et al. | |

It is certified that error appears in the above-identified patent and that said Letters Patent is hereby corrected as shown below:

On the title page, item (60), please add; --in the Related U.S. Application Data, line 1, Provisional application No. 60/692,230, filed on Jun. 21, 2005--.

Signed and Sealed this

Twenty-first Day of April, 2009

JOHN DOLL
*Acting Director of the United States Patent and Trademark Office*